United States Patent [19]

Atwal

[11] Patent Number: 5,276,168
[45] Date of Patent: Jan. 4, 1994

[54] BENZOPYRAN DERIVATIVES AND HETEROCYCLIC ANALOGS THEREOF AS ANTIISCHEMIC AGENTS

[75] Inventor: Karnail Atwal, Newtown, Pa.

[73] Assignee: E. R. Squibb & Sons, Inc., Princeton, N.J.

[21] Appl. No.: 901,443

[22] Filed: Jun. 19, 1992

Related U.S. Application Data

[63] Continuation-in-part of Ser. No. 630,472, Dec. 19, 1990, abandoned, which is a continuation-in-part of Ser. No. 540,423, Jun. 18, 1990, abandoned.

[51] Int. Cl.$^5$ ............................................. C07D 311/68
[52] U.S. Cl. ................................... 549/404; 549/399; 549/345; 549/220; 548/525; 548/413; 548/407; 546/196; 546/22; 546/15; 544/376; 544/151; 540/596
[58] Field of Search ............... 549/399, 404, 345, 220; 548/525, 413, 407; 546/196, 22, 15; 544/376, 151; 540/596

[56] References Cited

U.S. PATENT DOCUMENTS

| | | | |
|---|---|---|---|
| 4,575,511 | 3/1986 | Evans et al. | 514/456 |
| 4,687,779 | 8/1987 | Evans | 514/456 |
| 4,782,083 | 11/1988 | Cassidy et al. | 514/456 |
| 5,011,837 | 4/1991 | Atwal et al. | 514/227.8 |

FOREIGN PATENT DOCUMENTS

| | | |
|---|---|---|
| 168619 | 1/1986 | European Pat. Off. |
| 205292 | 12/1986 | European Pat. Off. |
| 322251 | 6/1989 | European Pat. Off. |
| 344747 | 12/1989 | European Pat. Off. |
| 412531 | 2/1991 | European Pat. Off. |
| WO85/00602 | 12/1985 | World Int. Prop. O. |

OTHER PUBLICATIONS

V. A. Ashwood et al., *J. Med. Chem.*, 1986; 29, 2194-2201.
A. Banerji et al., *Tetrahedron Letters*, No. 38, pp. 3685-3686, 1979.
J. M. Evans et al., *J. Med. Chem.*, 1983, 26, 1582-1589.
R. W. Lang et al., *Helvetica Chimica Acta.*, vol. 71 (1988) pp. 596-601.
G. Ariamala et al., *Tetrahedron Letters*, vol. 29, No. 28, pp. 3487-3488 (1988).
P. Sebok et al., *Heterocycles*, vol. 27, No. 11 (1988) pp. 2595-2607.
P. Teixidor et al., *Heterocycles*, vol. 27, No. 10, 1988, pp. 2459-2465.

*Primary Examiner*—Nicky Chan
*Attorney, Agent, or Firm*—Theodore R. Furman, Jr.; Ellen K. Park

[57] ABSTRACT

A new method for the treatment of ischemic conditions and arrhythmia is disclosed. The method uses compounds of the formula

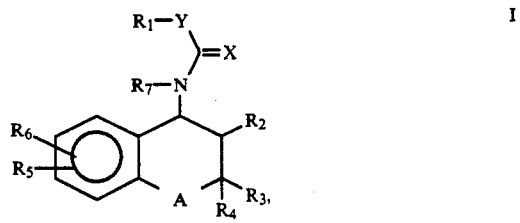

wherein A can be —$CH_2$—, —O—, —$NR_9$—, —S—, —SO—, —$SO_2$—; X can be oxygen or sulfur; Y can be —$NR_8$, —O—, —S—, —$CH_2$— and the R groups are as defined herein. Novel compounds within the definition of formula I are also disclosed.

7 Claims, No Drawings

BENZOPYRAN DERIVATIVES AND HETEROCYCLIC ANALOGS THEREOF AS ANTIISCHEMIC AGENTS

This is a continuation-in-part of U.S. Ser. No. 630,472 filed Dec. 19, 1990, now abandoned, which is a continuation-in-part of U.S. Ser. No. 540,423 filed Jun. 18, 1990, now abandoned.

FIELD OF THE INVENTION

The present invention relates to novel potassium channel activators and to a method of using these and other compounds having potassium channel activating activity as antiischemic and antiarrhythmic agents.

SUMMARY OF THE INVENTION

In accordance with the present invention a new method for using compounds having potassium channel activating activity as antiischemic and antiarrhythmic agents is disclosed. These compounds for use in the present method have the general formula

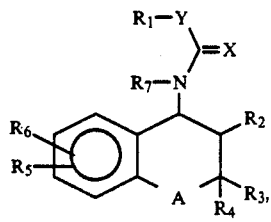

I or pharmaceutically acceptable salts thereof, wherein A can be $-CH_2-$, $-O-$, $-NR_9-$, $-S-$, $-SO-$ or $-SO_2-$, where $R_9$ is hydrogen or lower alkyl of 1 to 4 carbons;

wherein X is oxygen or sulfur;

Y is $-NR_8$, $-O-$, $-S-$ or $-\overset{R_{10}}{\underset{|}{CH}}-$;

$R_1$ is aryl, arylalkyl, heterocyclo or (heterocyclo)alkyl;
$R_2$ is hydrogen, hydroxy,

$R_3$ and $R_4$ are each independently hydrogen, alkyl or arylalkyl, or, $R_3$ and $R_4$ taken together with the carbon atom to which they are attached form a 5- to 7-membered carbocyclic ring;
$R_5$ is selected from H, alkyl, haloalkyl, alkenyl, alkynyl, cycloalkyl, arylalkyl, cycloalkylalkyl, $-CN$, $-NO_2$, $-COR$, $-COOR$, $-CONHR$, $-CON(R)_2$, $-CF_3$, S-alkyl, $-SOalkyl$, $-SO_2alkyl$,

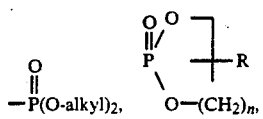

halogen, amino, substituted amino, O-alkyl, $OCF_3$, $OCH_2CF_3$, $-OCOalkyl$, $-OCONRalkyl$, $-NRCOal$- kyl and $NRCOOalkyl$, $NRCON(R)_2$ wherein R in each of the above groups can be hydrogen, alkyl, aryl, arylalkyl, cycloalkyl, or (cycloalkyl)alkyl or haloalkyl;

$R_6$ is selected from H, alkyl, halo, OH, O-alkyl, amino and substituted amino, O-alkyl, OCOalkyl, OCONRalkyl, NRCOalkyl and NRCOOalkyl, $NRCON(R)_2$ wherein R in each of the above groups can be hydrogen, alkyl, aryl, arylalkyl, cycloalkyl, (cycloalkyl)alkyl or haloalkyl;

$R_7$ and $R_8$ are each independently selected from hydrogen, alkyl, arylalkyl;

or $R_1$ and $R_8$, or $R_1$ and $R_7$, or $R_7$ and $R_8$ taken together can form a 5- to 7-membered saturated or unsaturated ring, which may further include an aryl group fused to 2 carbon atoms of such 5- to 7-membered ring;

n is 1, 2 or 3; and, $R_{10}$ is hydrogen, hydroxy, alkyl or O-alkyl.

Also disclosed are novel compounds which are the compounds of formula I with the proviso that when Y is $-NH$, $R_2$ is hydroxy, $R_3$ and $R_4$ are each methyl, $R_5$ is hydrogen, $R_6$ is 6-cyano, $R_7$ is hydrogen and A and X are each oxygen, $R_1$ must be other than phenyl.

DETAILED DESCRIPTION OF THE PRESENT INVENTION

This invention in its broadest aspects relates to a new method of using the compounds of formula I as antiischemic and antiarrhythmic agents and also to novel compounds of formula I.

The novel compounds of the present invention are all the compounds of formula I except those wherein Y is $-NH-$, $R_1$ is phenyl, $R_2$ is hydroxy, $R_3$ and $R_4$ are each methyl, $R_5$ is hydrogen, $R_6$ is 6-cyano, $R_7$ is hydrogen, and A and X are each oxygen. Preferred compounds are those with the 3S, 4R stereochemistry.

U.S. Pat. No. 4,575,511 discloses compounds of the formula

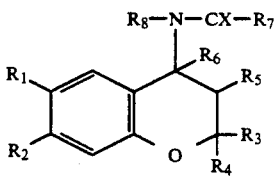

A where X is oxygen or sulfur and $R_7$ is selected from the class consisting of $C_{1-6}alkyl$ substituted by amino optionally substituted by one or two $C_{1-6}alkyl$ groups which may be the same or different; amino optionally substituted by a $C_{1-6}alkyl$ or $C_{1-6}alkenyl$ group or a $C_{1-6}alkanoyl$ group optionally substituted by up to three halo atoms or by a phenyl group optionally substituted by $C_{1-6}alkyl$, $C_{1-6}alkoxy$ or halogen, or $C_{1-6}alkoxy$ or phenoxy optionally substituted by $C_{1-6}alkyl$, $C_{1-6}alkoxy$ or halogen; or, when X is oxygen, $R_7$ is further selected from the class of carboxy. $C_{1-6}alkoxycarbonyl$, or aminocarbonyl optionally substituted by one or two $C_{1-6}alkyl$ groups which may be the same or different.

These compounds are disclosed as being antihypertensives. In fact, it has now been found that certain compounds in the '511 patent have little or no antihypertensive activity but, surprisingly, are useful as antiischemic agents. In particular, the compound of Example 3 of U.S. Pat. No. 4,575,511, shown as

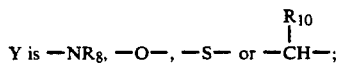

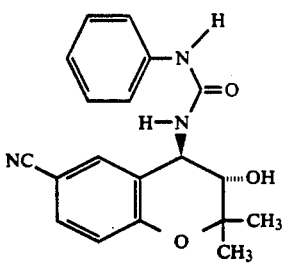

has been found to possess little or no antihypertensive activity but has antiischemic activity. Additionally, this and all the compounds of formula I are useful as antiarrhythmic agents.

The term "alkyl" used in defining various symbols refers to straight or branched chain saturated hydrocarbon radicals having up to eight carbons, preferably from one to five carbons. Similarly, the terms "alkoxy" and "alkylthio" refer to such alkyl groups attached to an oxygen or sulfur.

The term "alkenyl" refers to straight or branched chain hydrocarbon radicals having from two to eight carbons and one double bond, preferably three to five carbons. The term "alkynyl" refers to straight or branched chain hydrocarbon radicals having from two to eight carbons and one triple bond, preferably three to five carbons.

The term "cycloalkyl" refers to saturated carbocyclic rings of 3 to 7 carbon atoms with cyclopropyl, cyclopentyl and cyclohexyl being most preferred.

The term "halo" or "halogen" refers to chloro, bromo and fluoro.

The term "halo substituted alkyl" refers to such alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term "aryl" refers to phenyl, 1-naphthyl, 2-naphthyl or mono substituted phenyl, 1-naphthyl, 2-naphthyl wherein said substituent is alkyl of 1 to 4 carbons, (amino)alkyl, (substituted amino)alkyl, alkylthio of 1 to 4 carbons, alkoxy of 1 to 4 carbons, halo, nitro, cyano, hydroxy, amino, -NH-alkyl wherein alkyl is of 1 to 4 carbons, -N(alkyl)2 wherein alkyl is of 1 to 4 carbons, —CF3, -O(haloalkyl),

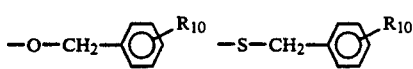

(wherein $R_{10}$ is hydrogen, alkyl of 1 to 4 carbons, alkoxy of 1 to 4 carbons, alkylthio of 1 to 4 carbons, halo, hydroxy or CF3), —O—CH2-cycloalkyl, —S—CH2-cycloalkyl, or -alkyl(COOR11) (where R11 is H or alkyl), and di-substituted phenyl, 1-naphthyl, 2-naphthyl wherein said substituents are selected from methyl, methoxy, methylthio, halo, CF3, nitro, amino, OCHF2, or -alkyl(COOR11) (where R11 is H or alkyl).

Preferred aryl groups include unsubstituted phenyl and monosubstituted phenyl wherein the substituents are nitro, halo, —CF3, alkyl, cyano, methoxy, or -alkyl(COOR11) (where R11 is H or alkyl).

The term "heterocyclo" refers to fully saturated or unsaturated rings of 5 or 6 atoms containing one or two O and S atoms and/or one to four N atoms provided that the total number of hetero atoms in the ring is 4 or less. The hetero ring is attached by way of an available atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxaiazolyl, and 4, 5, 6 or 7-benzofuranzanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, -NH-alkyl wherein alkyl is of 1 to 4 carbons, -N(alkyl)2 wherein alkyl is of 1 to 4 carbons, CF3, or OCHF2 or such monocyclic and bicyclic rings wherein two or three available carbons have substituents selected from methyl, methoxy, methylthio, halo, CF3, nitro, hydroxy, amino and OCHF2.

The term "substituted amino" refers to a group of the formula $-NZ_1Z_2$ wherein $Z_1$ is hydrogen, alkyl, cycloalkyl, aryl, arylalkyl, cycloalkylalkyl and $Z_2$ is alkyl, cycloalkyl, aryl, arylalkyl, cycloalkylalkyl or $Z_1$ and $Z_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diaryalkyl-1-piperazinyl, 1-pyrrolidinyl, 1-piperidinyl, or 1-azepinyl substituted with alkyl, alkoxy, alkylthio, halo, trifluoromethyl or hydroxy.

The compounds of formula I wherein A is oxygen, X is oxygen and Y is NR8 can be prepared by treatment of a compound of the formula

with 4-nitrophenylchloroformate to provide an intermediate of the formula

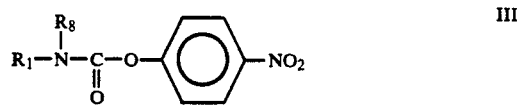

Intermediate III can thereafter be reacted with an amine of the formula

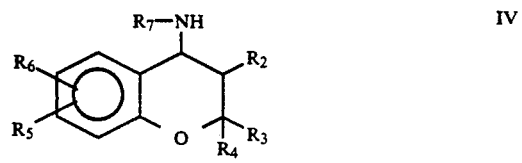

in an organic solvent, such as dimethylformamide, tetrahydrofuran, acetonitrile or dichloromethane, to provide the compounds of formula I where A and X are each oxygen and Y is NHR8.

Compounds of formula I wherein X is oxygen or sulfur and Y is $NR_8$ (where $R_8$ is hydrogen) can also be prepared from compound of formula IV by treatment with an isocyanate or isothiocyanate of the formula V

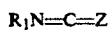

$R_1N=C=Z$ (Z=O, S).

Compounds of formula I wherein X, Y and A are oxygen can be prepared from a compound of formula IV by treatment with a chloroformate of the formula

VI in an organic solvent and in the presence of an amine catalyst.

Compounds of formula I wherein X and A are oxygen and Y is

can be prepared by reacting a compound of formula IV with an acid of the formula

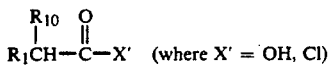

VII and a carbodiimide or an acyl chloride of formula VII in an organic solvent and a base such as triethylamine and pyridine.

Compounds of formula I wherein X is sulfur can be prepared by treating compounds of formula I wherein X is oxygen with Lawesson's reagent or with $P_4S_{10}$ in organic solvents such as tetrahydrofuran and toluene.

The aminoalcohol of formula IV wherein $R_2$ is trans hydroxy can be prepared by methods described in the literature, such as by J. M. Evans, C. S. Fake, T. C. Hamilton, R. H. Poyser, E. A. Watts, *J. Med. Chem.*, 1983, 26, 1582 and *J. Med. Chem.*, 1986, 29, 2194; R. W. Lang, P. F. Wenk, *Helvetica Chimica Acta*, 1988, 71, 596; EP 0205292 A2 (1986), and WO 87/07607. The amino alcohol of formula IV wherein A is —O— and $R_2$ is cis hydroxy can be prepared by methods described by G. Burrell, J. M. Evans, G. E. Jones and G. Stemp, *Tetrahedron Letters*, Vol. 31, p. 3649 (1990).

The amine of formula IV, wherein $R_2$ is hydrogen and A is —O—, can be prepared from a ketone of the formula

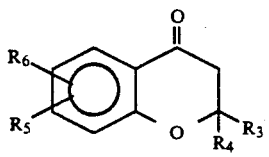

VIII by Standard methodology. The ketone of formula VIII can be obtained by literature procedures, such as disclosed by P. Sebok and T. Timar, *Heterocycles*, 1988, 27, 2595; P. Teixidor et al., *Heterocycles*, 1988, 27, 2459; A. Benerji and N. C. Goomer, *Tetrahedron Letters*, 1979, 3685; G. Ariamala and K. K. Subramanian, *Tetrahedron Letters*, Vol. 29, No. 28, p. 3487-3488 (1988).

The amine of formula IV wherein A is —O— and $R_2$ is hydrogen, can also be prepared from olefin of the formula

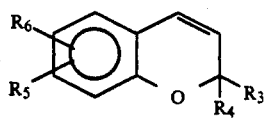

IX by a sequence of steps which involve: (a) catalytic hydrogenation of the double bond, (b) bromination of the resulting compound with N-bromosuccinimide and light, (c) displacement of the bromide with azide using sodium azide followed by (d) catalytic reduction of the azide.

Compounds of formula I wherein A is $CH_2$, $NR_9$, —S—, —SO— and —$SO_2$— can be prepared in a similar manner from amines of the formula

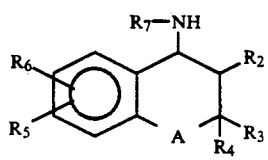

X wherein A is $CH_2$, $NR_9$, —S—, —SO—, —$SO_2$—.

Compounds of formula X where A is NH are described in WO 85/00602.

Compounds of formula X where A is S, —SO—, —$SO_2$— are described in EP 322-251-A.

Compounds of formula X wherein A is $CH_2$ can be prepared as described in EP-168-619-A.

Compounds of formula I wherein $R_1$ and $R_7$ are joined through a saturated ring, can be prepared by treatment of an intermediate of the formula

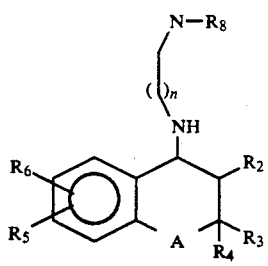

XI with 4-nitrophenylchloroformate and a base, such as triethylamine in an organic solvent, such as dichloromethane, acetonitrile, etc.

Compounds of formula XI, wherein $R_2$ is transhydroxyl, can be prepared by reacting an epoxide of the formula

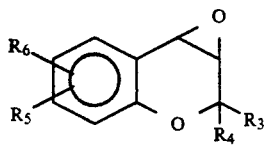

XII with an amine of the formula

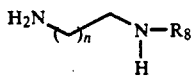
XIII in an alcoholic solvent such as ethanol.

The preparation of epoxide of formula XII is described by J. M. Evans, C. S. Fake, T. C. Hamilton, R. H. Poyser, E. A. Watts, *J. Med. Chem.*, 1983, 26, 1582 and *J. Med. Chem.*, 1986, 29, 2194; and R. W. Lang, P. F. Wenk, *Helvetica Chimica Acta*, 1988, 71, 596.

Compounds of formula XI can also be prepared by alkylation of an amine of formula IV with an alkylating agent of the formula

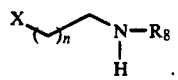
XIV

Compounds of formula I wherein $R_1$ and $R_7$ are joined through an aryl ring, can be prepared by cyclization of an intermediate of the formula

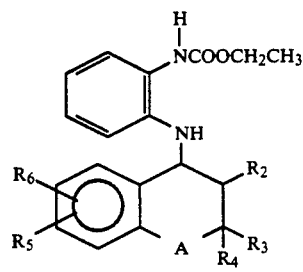
XV with a base such as sodium methoxide in methanol.

Compounds of formula XV can be prepared from epoxide XII and an aniline of the formula

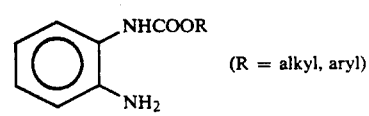
XVI (R = alkyl, aryl)

in the presence of magnesium perchlorate in an organic solvent such as acetonitrile.

Compounds of formula XVI are described in the literature, e.g., J. Davoll & D. H. Lancy, *J. Chem. Soc.*, p. 314 (1960).

For the preparation of individual enantiomers of compounds of formula I (wherein $R_2$=H, OH and A=O), compound IV ($R_2$==H, OH and A=O) is converted to diastereomeric amides of the formula

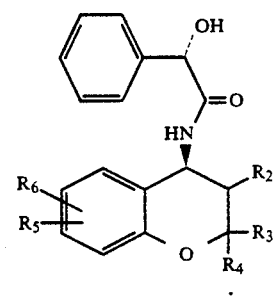
XVII and

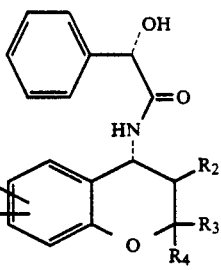
XVIII by treatment with chiral nonracemic mandelic acid in the presence of dicyclohexylcarbodiimide.

Compounds XVII and XVIII are separated by crystallization or chromatography. The enantiomer of mandelic acid that yields crystalline diastereomer with the desired 4R-stereochemistry of benzopyran (as shown in formula XV) is preferred in the resolution step.

Compounds XVII and XVIII are then hydrolyzed by heating in the presence of sulfuric acid in dioxane to give enantiomers of the formula

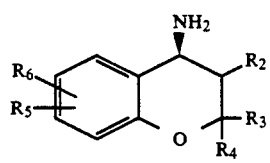
XIX and

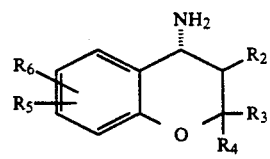
XX

The enantiomers XIX and XX are then converted to chiral nonracemic compounds of formula I. Similar technology can be utilized to prepare the corresponding enantiomers where A is other than oxygen.

The compounds of the present invention can have asymmetric centers at carbons 2–4 of benzopyran ring. Also, any one of the R's can have an asymmetric carbon. Consequently, compounds of formula I can exist in diastereomeric forms or in mixtures thereof. The above described process can utilize racemates, enantiomers or diastereomers as starting materials. When diastereomeric products are prepared, they can be separated by conventional chromatographic or fractional crystallization methods.

The compounds of the present invention wherein $R_7$ is hydrogen, Y is $NR_8$ and $R_8$ is hydrogen, can exist as a mixture of tautomers represented by the following structures. The tautomeric products are obtained in relative amounts that differ from compound to compound. All forms are included in the scope of formula I.

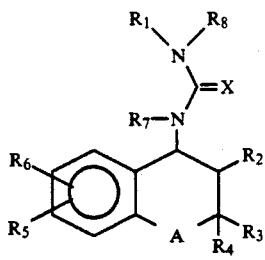

I'

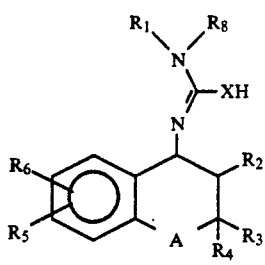

I''

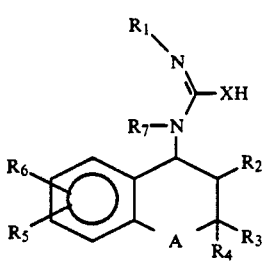

I'''

Tautomers of formula I similar to I' and I'' are also possible wherein Y is O, S and

$$\begin{array}{c} R_{10} \\ | \\ -CH- \end{array}$$

and are also included in the scope of this invention.

The compounds of formula I and the pharmaceutically acceptable salts act as potassium channel activators. Thus, compounds of the present invention are useful cardiovascular agents, e.g. as anti-arrhythmic agents and antiischemic agents.

As described previously, compounds of formula I are particularly useful as antiischemic agents since they have been found to possess little or no antihypertensive activity. Thus, compounds of formula I are useful for the treatment of ischemic conditions, e.g. myocardial ischemia, cerebral ischemia, lower limb ischemia and the like. The selectivity, i.e., antiischemic activity with little or no antihypertensive activity, means that in the treatment of, for example, ischemic heart, these compounds are less likely to cause coronary steal, profound hypotension and coronary underperfusion. By little or no vasodilation activity is meant that these compounds have $IC_{50}$ (rat aorta) values greater than that of the potassium channel activator, cromakalim. The "selective" antiischemic agents typically are those having $IC_{50}$ (rat aorta) values $>10$ times that of cromakalim (i.e., have 1/10 the vasodilatory action) and preferably those having $IC_{50}$ values $>50$ times that of cromakalim.

Thus, for example, by the administration of a composition containing one (or a combination) of the compounds of this invention, ischemic conditions of a mammalian (e.g., human) host are reduced. A single dose, or preferably two to four divided daily doses, provided on a basis of about 0.001 to 100 mg per kilogram of body weight per day, preferably from about 0.1 to about 25 mg per kilogram per day, is appropriate to reduce ischemic conditions. The substance is preferably administered orally, but parenteral routes, such as the subcutaneous, intramuscular, or intravenous routes or any other convenient delivery system, such as inhalation or intranasal solutions or transdermal patches, can also be employed. The above doses are also suitable for the other cardiovascular and non-cardiovascular uses.

As a result of the potassium channel activating activity of compounds of this invention, these compounds are also useful in the treatment of cardiovascular disorders. For example, compounds of the present invention are useful as therapy for congestive heart failure, as anti-anginal agents, as anti-fibrillatory agents, as thrombolytic agents and in limiting myocardial infarction.

Compounds of the present invention are additionally expected to be useful in the treatment of central nervous system disorders (e.g., Parkinsonism, as anti-tremor agents, epilepsy).

The compounds of this invention can also be formulated in combination with a diuretic such as, chlorothiazide, hydrochlorothiazide, flumethiazide, hydroflumethiazide, bendroflumethiazide, methylchlothiazide, trichloromethiazide, polythiazide or benzthiazide as well as ethacrynic acid, tricrynafen, chlorthalidone, furosemide, musolimine, bumetanide, triamterene, amiloride and spironolactone and salts of such compounds, angiotensin converting enzyme inhibitors such as captopril, zofenopril, fosinopril, enalapril, ceranopril, cilazopril, delapril, pentopril, quinapril, ramipril, lisinopril, and salts of such compounds, thrombolytic agents such as tissue plasminogen activator (tPA), recombinant tPA, streptokinase, urokinase, prourokinase, and anisoylated plasminogen streptokinase activator complex (APSAC, Eminase, Beecham Laboratories), or calcium channel blocking agents such as nifedipine or diltiazem. Such combination products if formulated as a fixed dose employ the compounds of this invention within the dose range described above and the other pharmaceutically active agent within its approved dose range.

The compounds of formula I, and combinations thereof, can be formulated, as described above, in compositions such as tablets, capsules or elixirs for oral administration, in sterile solutions or suspensions for parenteral administration, and may also be administered via transdermal patch or nasal inhalation solutions. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Preferred compounds are those wherein

A is —O—;
X is O, S;
Y is NH, $CH_2$;
$R_1$ is aryl, arylalkyl, heterocyclo, heterocyclo(alkyl);
$R_2$ is hydroxy, hydrogen;
$R_3$ and $R_4$ are each alkyl;
$R_5$ is an electron withdrawing group;
$R_6$ is hydrogen, alkyl, O-alkyl; and,
$R_7$ is hydrogen;
$R_1$ and $R_7$ taken together form a 5-6 membered ring and Y is N-aryl;

$R_1$ and $R_7$ are together part of an aryl ring and Y is NH.

Most preferred are those compounds wherein

A is —O—;
X is O;
Y is NH;
$R_1$ is phenyl, phenylmethyl, 2-, 3- or 4-pyridyl, 2-, 3- or 4-pyridylmethyl;
$R_2$ is trans-hydroxy, hydrogen;
$R_3$ and $R_4$ are each methyl;
$R_5$ is —CN or —NO$_2$;
$R_6$ is hydrogen; and,
$R_7$ is hydrogen;
$R_1$ and $R_7$ taken together form a 5-membered saturated ring and Y is N-phenyl;
$R_1$ and $R_7$ are together part of an aryl ring and Y is NH.

Specific embodiments of the present invention are described hereinafter in the following examples.

EXAMPLE 1

(trans)-1-(6-Cyano-3,4-dihydro-3-hydroxy-2,2-dimethyl-2H-1-benzopyran-4-yl)-3-phenylurea A suspension of (trans)-4-amino-3,4-dihydro-3-hydroxy-2,2-dimethyl-2H-1-benzopyran-6-carbonitrile (prepared according to Evans et al., *J. Med. Chem.*, 1983, 26, p. 1582 and *J. Med. Chem.*, 1986, 29, p. 2194) (1.0 g, 4.6 mmol) in ethanol (4 ml) under argon was treated with phenylisocyanate (0.55 g, 4.6 mmol) and the reaction was heated at reflux temperature for 4 hours. The product precipitate out of the reaction. The reaction was then concentrated in vacuo and the residue was triturated with isopropylether to give the title compound as a colorless solid (0.9 g, 63%), m.p. 240–241° C.: $^1$H NMR (CDCl$_3$/DMSO) δ 8.3 (s, 1 H), 7.7 (s, 1 H), 7.4 (d, J=8.0 Hz, 3 H), 7.26 (t, J=8.0 Hz, 2 H), 7.0 (t, J=9.0 & 7.0 Hz, 1 H), 6.86 (d, J=9.0 Hz, 1 H), 6.4 (d, J=8.0 Hz, 1 H), 5.3 (d, J=5.0 Hz, 1 H), 4.9 (t, J=9.0 & 8.0 Hz, 1 H), 3.6 (dd, J=4.0 & 6.0 Hz, 1 H), 1.5 (s, 3 H), 1.3 (s, 3 H); $^{13}$C NMR (CDCl$_3$/DMSO) 157.0, 156.5, 139.1, 132.2, 132.1, 128.4, 123.9, 121.8, 118.2, 117.8, 80.0, 74.3, 49.9, 26.1, 18.4; IR (KBr) 1132, 1267, 1491, 1550, 1612, 1645, 2226, 2932, 2978, 3433 cm$^{-1}$.

Analysis calc'd for C$_{19}$H$_{19}$N$_3$O$_3$:
C, 67.64; H, 5.68; N, 12.45; Found: C, 67.35; H, 5.45; N, 12.35.

EXAMPLE 2

(trans)-1-(6-Cyano-3,4-dihydro-3-hydroxy-2,2-dimethyl-2H-1-benzopyran-4-yl)-3-phenylthiourea A suspension of (trans)-4-amino-3,4-dihydro-3-hydroxy-2,2-dimethyl-2H-1-benzopyran-6-carbonitrile (prepared according to Evans et al., *J. Med. Chem.*, 1983, 26, p. 1582 and *J. Med. Chem.*, 1986, 29, p. 2194) (1.0 g, 4.6 mmol) in ethanol (4 ml) under argon was treated with phenylisothiocyanate (0.62 g, 4.6 mmol) and the reaction was heated at reflux for 4 hours. The reaction was then concentrated in vacuo and the residue was triturated with isopropylether to give the title compound as a colorless solid (1.4 g, 85%), m.p. 183–185° C.; $^1$H NMR (CDCl$_3$) δ 8.5 (s, 1 H), 7.4 (m, 7 H), 6.83 (d, J=8.0 Hz, 1 H), 6.1 (s, 1 H), 6.0 (s, 1 H), 4.0 (s, 1 H), 3.67 (d, J=10.0 Hz, 1 H), 1.5 (s, 3 H), 1.3 (s, 3 H); $^{13}$C NMR (CDCl$_3$) 182.5, 156.8, 133.3, 131.9, 130.4, 128.2, 126.0, 125.8, 122.2, 118.8, 118.6, 104.0, 80.5, 75.8, 50.0, 26.3, 18.6; IR (KBr) 1070, 1265, 1491, 1531, 2226, 2978, 3312, 3362 cm$^{-1}$.

Analysis calc'd for C$_{19}$H$_{19}$N$_3$O$_2$S:
C, 64.56; H, 5.42; N, 11.89; S, 9.07; Found: C, 64.50; H, 5.41; N, 11.64; S, 8.76.

EXAMPLE 3 trans-1-N-(6-Cyano-3,4-dihydro-3-hydroxy-2,2-dimethyl-2H-1-benzopyran-4-yl)benzeneacetamide To a solution of (trans)-4-amino-3,4-dihydro-3-hydroxy-2,2-dimethyl-2H-1-benzopyran-6 carbonitrile, hydrochloride (prepared according to Evans et al., *J. Med. Chem.*, 1983, 26, p. 1582 and *J. Med. Chem.*, 1986, 29, p. 2194) (1.0 g, 3.9 mmole) in 20% aqueous tetrahydrofuran (25 mL) was added phenylacetylchloride (0.91 g, 5.9 mmole, 0.8 mL) dropwise. The pH of the reaction mixture was maintained between 8.5-9.0 by simultaneous addition of 25% aqueous sodium carbonate solution. After completion of addition, the reaction mixture was stirred for one more hour. It was then diluted with ethyl acetate (200 mL) and the layers were separated. Organic layer was washed with water, dried and concentrated in vacuo to give 1.1 g (84%) of product. The crude solid was recrystallized from chloroform to give the title compound (0.7 g) as a white solid, m.p. 204–205° C.: $^1$H NMR (DMSO-d$_6$) δ 8.55 (d, J=8.0 Hz, 1 H), 7.6 (dd, J=1.0 & 9.0 Hz, 1 H), 7.35 (m, 6 H), 6.95 (d, J=9.0 Hz, 1 H), 5.7 (d, J=6.0 Hz, 1 H), 4.85 (t, J=10.0 & 9.0 Hz, 1 H), 3.6 (m, 3 H), 1.4 (s, 3 H), 1.2 (s, 3 H); $^{13}$C NMR (DMSO-d$_6$) 171.5, 156.5, 136.5, 132.8, 129.3, 128.5, 126.8, 125.4, 119.1, 118.1, 103.0, 80.6, 71.3, 48.8, 43.0, 26.8, 19.1; IR (KBr) 1071, 1126, 1268, 1489, 1652, 2225, 2976, 3411 cm$^{-1}$.

Analysis calc'd for C$_{20}$H$_{20}$N$_2$O$_3$ .0.1 H$_2$O:
C, 71.02; H, 6.02; N, 8.28; Found: C, 70.94; H, 5.94; N, 8.05.

EXAMPLE 4

[3R-[3α,4β(S*)]]-N-(6-Cyano-3,4-dihydro-3-hydroxy-2,2-dimethyl-2H-1-benzopyran-4-yl)-α-hydroxybenzeneacetamide To a solution of (trans)-4-amino-3,4-dihydro-3-hydroxy-2,2-dimethyl-2H-1-benzopyran-6-carbonitrile (prepared according to Evans et al., *J. Med. Chem.*, 1983, 26, p. 1582 and *J. Med. Chem.*. 1986, 29, p. 2194) (10.0 g, 45.9 mmol), S-(+)-mandelic acid (6.98 g, 45.9 mmol), hydroxybenzotriazole hydrate (6.2 g, 45.9 mmol) in dimethylformamide (60 ml) at 0° C. was added dicyclohexylcarbodiimide (9.5 g, 45.9 mmol). It was allowed to stir at room temperature for 20 hours and then cooled in an ice bath. The precipitated solid was filtered and the filtrate was concentrated in vacuo. The residue was dissolved in 5 percent methanol in chloroform and washed with 1N sodium hydroxide, 1N hydrochloric acid, brine and dried over anhydrous magnesium sulfate. After removing drying agent, the solvent was removed in vacuo. The residue was crystallized from ethanol to give the title compound (6.0 g) as a white solid, m.p. 238–240° C., $[\alpha_D]^{25} = +94.6°$ (c=1, MeOH): $^1$H NMR (CDCl$_3$) δ 7.4 (m, 5 H), 7.26 (t, J=1.0 Hz, 1 H), 6.97 (d, J=9.0 Hz, 1 H), 6.83 (d, J=9.0 Hz, 1 H), 5.16 (s, 1 H), 4.98 (t, J=9.0 Hz, 1 H), 3.8 (d, J=5.0 Hz, 1 H), 3.55 (dd, J=4.0 & 5.0 Hz, 1 H), 1.45 (s, 3 H), 1.2 (s, 3 H).

Analysis calc'd for C$_{20}$H$_{20}$N$_2$O$_4$:
C, 68.17; H, 5.72; N, 7.95; Found: C, 67.92; H, 5.49; N, 8.05.

EXAMPLE 5

3S-[3α,4β(R*)]]-N-(6-Cyano-3,4-dihydro-3-hydroxy-2,2-dimethyl-2H-1-benzopyran-4-yl)-α-hydroxybenzeneacetamide The residual material of the mother liquor of Example 4 above was purified by flash chromatography on silica gel eluting with hexane-ethyl acetate mixture (3:7) and the residue was crystallized from dichloromethane-isopropyl ether to give the title compound (6.0 g) as a white solid, m.p. 100–102° C. (foaming); $[\alpha_D]^{25} = -26.1°$ (c = 1, MeOH): $^1$H NMR (DMSO-d$_6$) δ 8.45 (d, J = 8.0 Hz, 1 H), 7.5 (m, 4 H), 7.3 (m, 2 H), 7.0 (s, 1 H), 6.88 (d, J = 8.0 Hz, 1 H), 6.2 (s, 1 H), 5.57 (d, J = 5.0 Hz, 1 H), 5.0 (s, 1 H), 4.76 (t, J = 9.0 Hz, 1 H), 3.75 (dd, J = 4.0 & 5.0 Hz, 1 H), 1.40 (s, 3 H), 1.15 (s, 3 H).

Analysis calc'd for $C_{20}H_{20}N_2O_4 \cdot 0.25\ H_2O$:

C, 67.30; H, 5.78; N, 7.84; Found: C, 67.54; H, 5.95; N, 7.44.

EXAMPLE 6

[3S-[3α,4β(S*)]]-N-(6-Cyano-3,4-dihydro-3-hydroxy-2,2-dimethyl-2H-1-benzopyran-4-yl)-α-hydroxybenzeneacetamide To a solution of (trans)-4-amino-3,4-dihydro-3-hydroxy-2,2-dimethyl-2H-1-benzopyran-6-carbonitrile (prepared according to Evans et al., *J. Med. Chem.*, 1983, 26, p. 1582 and *J. Med. Chem.*, 1986, 29, p. 2194) (1.64 g, 7.5 mmol), R(−)-mandelic acid (1.14 g, 7.5 mmol), hydroxybenzotriazole hydrate (1.0 g, 7.5 mmol) in dimethylformamide (15 ml) at 0° C. was added dicyclohexylcarbodiimide (1.55 g, 7.5 mmol) at room temperature. The reaction mixture was allowed to stir at room temperature for 20 hours and then cooled in an ice bath. The solid was removed by filtration and the filtrate was concentrated in vacuo. The residue was dissolved in 5% methanol in chloroform and washed with 1N sodium hydroxide, 1N hydrochloric acid, brine followed by drying over anhydrous magnesium sulfate. After removing drying agent the solvent was removed in vacuo. The residue was crystallized from ethanol to give the title compound (0.85 g) as a white solid, m.p. 235–237° C.: $[\alpha_D]^{25} = -94.9°$ (c = 1, MeOH); $^1$H NMR (DMSO-d$_6$) δ 8.45 (d, J = 8.0 Hz, 1 H), 7.5 (m, 4 H), 7.3 (m, 2 H), 7.0 (s, 1 H), 6.88 (d, J = 8.0 Hz, 1 H), 6.2 (s, 1 H), 5.57 (d, J = 5.0 Hz, 1 H), 5.0 (s, 1 H), 4.76 (t, J = 9.0 Hz, 1 H), 3.75 (dd, J = 4.0 & 5.0 Hz, 1 H), 1.40 (s, 3 H), 1.15 (s, 3 H).

Analysis calc'd for $C_{20}H_{20}N_2O_4$:

C, 68.17; H, 5.72; N, 7.95; Found: C, 68.00; H, 5.52; N, 7.95.

EXAMPLE 7

[3R-[3α,4β(R*)]]-N-(6-Cyano-3,4-dihydro-3-hydroxy-2,2-dimethyl-2H-1-benzopyran-4-yl)-α-hydroxybenzene-acetamide The residual material recovered from the mother liquor of Example 6 above was purified by flash chromatography on silica gel eluting with hexane-ethyl acetate (3:7) and the product was crystallized from dichloromethane-isopropyl ether to give the title compound as a white solid, m.p. 100–102° C. (foaming): $[\alpha_D]^{25} = +25.6°$ (c = 1, MeOH): $^1$H NMR (CDCl$_3$) δ 7.4 (m, 5 H), 7.26 (t, J = 1.0 Hz, 1 H), 6.97 (d, J = 9.0 Hz, 1 H), 6.83 (d, J = 9.0 Hz, 1 H), 5.16 (s, 1 H), 4.98 (t, J = 9.0 Hz, 1 H), 3.8 (d, J = 5.0 Hz, 1 H), 3.55 (dd, J = 4.0 & 5.0 Hz, 1 H), 1.45 (s, 3 H), 1.2 (s, 3 H).

Analysis calc'd for $C_{20}H_{20}N_2O_4 \cdot 0.25\ H_2O$:

C, 67.30; H, 5.78; N, 7.84; Found: C, 67.17; H, 5.87; N, 7.44.

EXAMPLE 8

N-(6-Cyano-3,4-dihydro-2,2-dimethyl-2H-1-benzopyran-4-yl)-N'-phenylurea

A. 6-Cyano-3,4-dihydro-2,2-dimethyl-2H-1-benzopyran

A solution of 6-cyano-2,2-dimethyl-2H-1-benzopyran (5.5 g, 29.7 mmoles, prepared according to Evans et al., *J. Med. Chem.*. 1983, 26, p. 1582 and *J. Med. Chem.*, 1986, 29, p. 2194) in anhydrous ethanol (40 ml) was treated with palladium on carbon (0.35 g) and stirred under hydrogen gas for 2 hours. The catalyst was filtered through a Celite and the filter cake washed with ethyl acetate. The filtrate was concentrated under vacuum to obtain 5.71 g of a yellow oil. The crude product was dissolved in ethyl acetate (60 ml) and washed successively with 5% hydrogen chloride solution (60 ml), saturated sodium hydrogen carbonate solution (60 ml), saturated sodium chloride solution (60 ml) and dried over anhydrous magnesium sulfate. The solvent was recovered under vacuum to yield 5.14 g of the title A compound as a yellow solid which was used in the next step without further purification. $^1$H NMR (CDCl$_3$) δ 7.37 (s, 1H), 7.34 (s, 1 H), 6.80 (d, J = 8.8 Hz, 1 H), 2.78 (dd, 2 H), 1.80 (dd, 2 H), 1.35 (s, 6 H). $^{13}$C NMR (CDCl$_3$) δ 157.95, 133.82, 131.34, 122.07, 119.53, 118.24, 102.66, 75.76, 32.13, 26.81, 22.06.

B. 4-Bromo-6-cyano-3,4-dihydro-2,2-dimethyl-2H-1-benzopyran

To a solution of the title A compound (6.40 g, 34.18 mmoles) in carbon tetrachloride (90 ml) was added N-bromosuccinimide (6.69 g, 37.6 mmoles, 1.1 eq.). The solution was purged with argon. A solution of azobisisobutyronitrile (0.4 g, 3.42 mmoles) in carbon tetrachloride (10 ml) was added; the reaction was heated at reflux for one-half hour with irradiation (high intensity visible light). The reaction mixture was concentrated under vacuum and the residue was dissolved in ethyl acetate (75 ml). The solution was washed successively with distilled water (4×75 ml), saturated sodium hydrogen carbonate solution (75 ml), saturated sodium chloride solution (75 ml), and dried over anhydrous magnesium sulfate. The solvent was recovered under vacuum to obtain 9.51 g of an orange waxy solid which was triturated with cold pentane to provide 7.19 g of a beige solid. This was crystallized from 10% ethyl acetate in hexane (25 ml) to yield 4.60 g of the title B compound as off-white needles. The mother liquors were combined and chromatographed on silica gel eluting with hexane/ethyl acetate (19:1) to afford an additional 2.26 g of product. $^1$H NMR (CDCl$_3$) δ 7.86 (d, J = 1.17 Hz, 1 H), 7.42 (dd, J = 1.76 and 8.79 Hz, 1 H), 6.82 (d, J = 8.80 Hz, 1 H), 5.35 (dd, 1 H), 2.45 (m, 2 H), 1.51 (s, 3 H), 1.31 (s, 3 H). $^{13}$C NMR (CDCl$_3$) δ 156.71, 136.25, 133.21, 122.61, 118.87, 103.81, 76.54, 43.57, 40.34, 28.36, 25.45.

C. 4-Azido-6-cyano-3,4-dihydro-2,2-dimethyl-2H-1-benzopyran

A solution of the title B compound (6.73 g, 25.29 mmoles) in dry N,N-dimethylformamide (100 ml) was treated with sodium azide (3.29 g, 50.57 mmoles, 2 eq.) and stirred at room temperature under argon for 4 hours. The reaction mixture was partitioned between ethyl acetate (100 ml) and distilled water (200 ml). The organic layer was separated and the aqueous layer was extracted with ethyl acetate (100 ml). The combined organics were washed successively with distilled water, saturated sodium hydrogen carbonate solution, saturated sodium chloride solution and dried over anhydrous magnesium sulfate. The solvent was evaporated under vacuum to obtain 5.62 g of orange gum which was triturated with pentane to provide 4.50 g of the title C compound as an off-white solid. $^1$H NMR (CDCl$_3$) δ 7.69 (s, 1 H), 7.46 (d, J=8.80 Hz, 1 H), 6.86 (d, J=8.21 Hz, 1 H), 4.59 (dd, J=6.45 and 2.34 Hz, 1 H), 2.24 (m, 1 H), 2.01 (m, 1 H), 1.49 (s, 3 H), 1.36 (s, 3 H). $^{13}$C NMR (CDCl$_3$) δ 157.66, 133.79, 133.41, 121.20, 119.24, 104.21, 76.80, 53.73, 38.30, 28.97, 26.29.

D.
4-Amino-6-cyano-3,4-dihydro-2,2-dimethyl-2H-1-benzopyran

A solution of the title C compound (2.00 g, 8.77 mmole) in absolute ethanol (50 ml) was treated with palladium on carbon (0.25 g) and stirred under hydrogen gas for 1.25 hours at room temperature. The reaction mixture was filtered to remove the catalyst. The filtrate was acidified to pH 1-2 with concentrated hydrogen chloride (0.85 ml) and concentrated under vacuum to a white solid. The crude amine hydrochloride was dissolved in distilled water (100 ml) and extracted with ethyl acetate (discarded). The aqueous layer was adjusted to pH 11-12 with 50% sodium hydroxide solution and extracted with ethyl acetate. The extracts were washed with saturated sodium chloride solution and dried over sodium sulfate. The solvent was evaporated under vacuum to provide 1.542 g of the title D compound as a yellow oil which solidified upon standing. The product was used in the next step without further purification. $^1$H NMR (DMSO-d$_6$) δ 8.01 (s, 1 H), 7.51 (d, J=8.21, 1 H), 6.82 (d, J=8.21, H), 3.86 (dd, 1 H), 2.07 (dd, J=5.87 and 13.49 Hz, 1 H), 1.56 (m, 1 H), 1.39 (s, 3 H), 1.24 (s, 3 H). $^{13}$C NMR (DMSO-d$_6$) δ 156.82, 132.51, 131.59, 129.40, 119.47, 117.45, 101.70, 76.99, 43.13, 42.47, 29.39, 24.70.

E.
N-(6-Cyano-3,4-dihydro-2,2-dimethyl-2H-1-benzopyran-4-yl)-N'-phenylurea A solution of the title D compound (0.70 g, 3.46 mmoles) and phenyl isocyanate (0.41 g, 3.46 mmoles) in anhydrous ethanol (11.5 ml) was heated at reflux for 1 hour and cooled to room temperature. The reaction product precipitated from solution. It was collected by suction filtration, washed with diisopropyl ether and dried under vacuum to obtain 0.743 g of the title compound as a white solid, m.p. 214-215° C. $^1$H NMR (CDCl$_3$) δ 8.60 (s, 1 H), 7.67 (s, 1 H), 7.62 (d, J=8.80 Hz, 1 H), 7.48 (s, 1 H), 7.45 (s, 1 H), 7.26 (m, 2 H), 6.94 (m, 2 H), 6.64 (d, J=8.21 Hz, 1 H), 5.00 (m, 1 H), 2.19 (m, 1 H), 1.76 (m, 1 H), 1.44 (s, 3 H), 1.32 (s, 3 H). $^{13}$C NMR (CDCl$_3$) δ 157.31, 155.23, 140.20, 132.46, 132.11, 128.68, 125.37, 121.34, 119.18, 118.14, 117.86, 102.10, 77.22, 41.86, 38.87, 28.96, 24.56.

Analysis calc'd for C$_{19}$H$_{19}$N$_3$O$_2$:
C, 71.01; H, 5.96; N, 13.07; Found: C, 71.14; H, 5.97; N, 12.91.

EXAMPLE 9
N-(6-Cyano-3,4-dihydro-2,2-dimethyl-2H-1-benzopyran-4-yl)-N'-(phenylmethyl)urea A solution of the title D compound from Example 8 (0.50 g, 2.47 mmoles) and benzyl isocyanate (0.33 g, 2.47 mmoles) in anhydrous ethanol (4 ml) was heated at reflux for 3 hours and cooled to room temperature. The reaction product precipitated from solution. It was collected by suction filtration; the solid was triturated with diisopropyl ether and dried under vacuum to obtain 0.71 g of the title compound as a white solid, m.p. 168-169° C. $^1$H NMR (DMSO-d$_6$) δ 7.59 (s, 1 H), 7.56 (s, 1 H), 7.38-7.24 (m, 5 H) 6.89 (d, J=8.21 Hz, 1 H), 6.56 (t, J=5.87 Hz, 1 H), 6.50 (d, J=8.21 Hz, 1 H), 4.94 (M, 1 H), 4.30 (d, J=5.86 Hz, 2 H), 2.10 (m, 1 H), 1.74 (m, 1 H), 1.41 (s, 3 H), 1.28 (s, 3 H). $^{13}$C NMR (DMSO-d$_6$) δ 158.11, 157.19, 140.78, 132.25, 132.08, 128.22, 126.93, 126.61, 126.12, 119.18, 118.03, 102.02, 77.28, 43.01, 41.95, 38.81, 29.08, 24.42.

Analysis calc'd for C$_{20}$H$_{21}$N$_3$O$_2$:
C, 71.62; H, 6.31; N, 12.53; Found: C, 71.56; H, 6.40; N, 12.29.

EXAMPLE 10
(trans)-1-(6-(Cyano-3,4-dihydro-3-hydroxy-2,2-dimethyl-2H-1-benzopyran-4-yl)-3-phenylmethyl)urea A suspension of (trans)-4-amino-3,4-dihydro-3-hydroxy-2,2-dimethyl-2H-1-benzopyran-6-carbonitrile (1.0 g, 4.6 mmol, prepared according to Evans et al. *J. Med. Chem.*, 1983, 26, p. 1582 and *J. Med. Chem.*, 1986, 29, p. 2194) in ethanol (4 ml) under argon was treated with benzylisocyanate (0.6 g, 4.6 mmol) and the reaction was heated at reflux temperature for 4 hours. The product precipitated out of the reaction. The reaction was then concentrated in vacuo and the residue was triturated with isopropyl ether to give the title compound as a colorless solid (1.3 g), m.p. 147-148° C. $^1$H NMR (DMSO) δ 7.60 (d, J=2.4, 1 H), 7.52 (s, 1 H), 7.35 (m, 3 H), 6.90 (d, J=8.8 Hz, 1 H), 6.59 (t, J=5.9 & 6.4 Hz, 1 H), 6.50 (d, J=8.2 Hz, 1 H), 5.67 (d, J=5.9 Hz, 1 H), 4.64 (t, J=9.3 & 8.8 Hz, 1 H), 4.3 (m, 2 H), 3.52 (dd, J=3.5 & 5.9 Hz, 1 H), 1.40 (s, 3 H), 1.17 (s, 3 H); $^{13}$C NMR (DMSO) 158.8, 156.2, 140.8, 132.7, 132.3, 128.2, 126.9, 126.6, 119.1, 117.8, 102.5, 80.3, 71.7, 49.5, 43.0, 26.5, 18.8; IR (KBr) 1266.5, 1305.8, 1489.5, 1566.1, 1611.5, 1634.8, 2226.4, 2979.3, 3355.0 cm$^{-1}$.

Analysis calc'd for C$_{20}$H$_{21}$N$_3$O$_3$:
C, 68.36; H, 6.02; N, 11.96; Found: C, 68.38; H, 6.02; N, 11.89.

EXAMPLE 11
(trans)-N-[3-(acetyloxy)-6-cyano-3,4-dihydro-2,2-dimethyl-2H-1-benzopyran-4-yl]-N'-phenylurea A solution of the title compound of Example 1 (2.70 g, 8.0 mmoles) and acetic anhydride (2.04 g, 20.0 mmoles) in pyridine (30 ml) was stirred at room temperature for four days. The reaction mixture was partitioned between 10% aqueous hydrogen chloride and ethyl acetate. The organic phase was washed with distilled water followed by saturated sodium chloride solution. The solvent was recovered under vacuum; the white solid (2.78 g, m.p. 263-264° C.) obtained was dried by co-evaporation with ethanol. $^1$H NMR (DMSO-d$_6$) δ 8.65 (s, 1 H), 7.66 (m, 2 H), 7.46 (s, 1 H), 7.43 (s, 1 H), 7.26 (m, 2 H), 7.02 (d, J=7.62, 1 H), 6.94

(m, 1 H), 6.67 (d, J=8.79, 1 H), 5.17 1d, J=8.79), 4.96, (t, J=8.79, 1 H), 2.09 (s, 3 H), 1.38 (s, 3 H), 1.30 (s, 3 H). $^{13}$C NMR (DMSO-d$_6$) δ 169.72, 155.84, 155.18, 140.11, 132.86, 132.66, 128.65, 124.62, 121.43, 118.84, 118.17, 117.94, 103.2, 78.35, 72.42, 47.16, 25.65, 20.64, 20.15.

Analysis calc'd for $C_{21}H_{21}N_3O_4$:

C, 66.48; H, 5.58; N, 11.07; Found: C, 66.32; H, 5.52; N, 11.06.

EXAMPLE 12

(trans)-1-(6-Acetyl-3,4-dihydro-3-hydroxy-2,2-dimethyl-2H-1-benzopyran-4-yl)-3-phenylurea

A.

6-Acetyl-3,4-dihydro-2,2-dimethyl-2H-1-benzopyran

To a solution of 95% 4-hydroxyacetophenone (13.6 g, 100 mmol), 3-chloro-3-methyl butyne (17.4 g, 170 mmol) in methylene chloride (75 ml) was added water (75 ml), sodium hydroxide (6.4 g, 160 mmol), and Triton B (40% in methanol, 23.0 g, 52 mmol). The reaction mixture was stirred at room temperature for six days. The organic layer was separated, the aqueous phase was reextracted with methylene chloride (2×200 ml). The combined extracts were concentrated in vacuo, the residue was taken up in ethyl acetate (500 ml) washed with 1N sodium hydroxide (3×250 ml), brine (200 ml) and dried over magnesium sulfate. The solvent was evaporated in vacuo and the residue was dissolved in 1,2-dichlorobenzene (40 ml) and heated at reflux temperature for four hours. The solvent was removed by distillation at atmospheric pressure using a vigreaux column and the residue was distilled under reduced pressure (b.p. 140-150° C. at 2.0 mm) to provide the title A compound (7.0 g) as a light yellow solid. $^1$H NMR (CDCl$_3$) δ 7.75 (dd, J=2.3 & 8.8 Hz, 1 H), 7.73 (d, J=2.4 Hz, 1 H), 6.78 (d, J=8.8 Hz, 1 H), 6.35 (d, J=10.0 Hz, 1 H), 5.66 (d, J=9.9 Hz, 1 H), 2.53 (s, 3 H), 1.45 (s, 6 H); $^{13}$C NMR (CDCl$_3$) δ 196.7, 157.4, 131.1, 130.2, 126.8, 121.6, 120.6, 116.0, 77.5, 28.3, 26.2.

B.

6-Acetyl-3,4-dihyro-2,2-dimethyl-3-bromo-4-hydroxy-2H-1-benzopyran

To a solution of the title A compound (2.0 g, 10 mmol) in dimethylsulfoxide/water (30:3 ml) was added N-bromosuccinimide (1.9 g, 10.8 mmol) in one portion at room temperature. The reaction mixture was stirred for 30 minutes at room temperature. It was then poured into water (50 ml) and extracted with ethyl acetate (2×100 ml). The organic layer was washed with water, dried over anhydrous magnesium sulfate and concentrated in vacuo to give a colorless residue which was triturated with isopropyl ether-hexanes to give the title B compound (2.5 g) as a white solid, m.p. 84-86° C. $^1$H NMR (CDCl$_3$) δ 8.15 (s, 1 H), 7.83 (dd J=2.3 & 6.5 Hz, 1 H), 6.85 (d, J=8.7 Hz, 1 H), 4.95 (d, J=9.4 Hz, 1 H), 4.14 (d, J=9.4 Hz, 1 H), 3.0 (m, 1 H), 2.56 (s, 3 H), 1.64 (s, 3 H), 1.43 (s, 3 H); $^{13}$C NMR (CDCl$_3$) δ 197.1, 156.5, 131.0, 130.5, 129.5, 122.4, 117.5, 80.2, 70.0, 62.1, 28.9, 26.7, 20.6.

C.

6-Acetyl-3,4-dihydro-2,2-dimethyl-3-hydroxy-4-amino-2H-1-benzopyran

To a solution of the title B compound (2.5 g, 8.4 mmol) in ethanol (20 ml) was added concentrated ammonium hydroxide solution (20 ml). The reaction mixture was heated in a pressure (closed) bottle for 4 hours. It was then concentrated in vacuo and triturated with ether to give the title C compound (1.9 g) as a colorless solid, m.p. 232-233° C. $^1$H NMR (DMSO) δ 8.34 (s, 1 H), 7.75 (dd, J=2.3 & 6.5 Hz, 1 H), 6.82 (d, J=8.8 Hz, 1 H), 4.10 (d, J=9.4 Hz, 1 H), 3.64 (d, J=9.4 Hz, 1 H), 2.49 (s, 3 H), 1.41 (s, 3 H), 1.10 (s, 3 H); $^{13}$C NMR (CDCl$_3$) δ 195.7, 156.3, 129.8, 129.0, 122.4, 118.0, 117.2, 79.1, 70.8, 50.4, 26.3, 26.2, 17.9.

D.

(trans)-1-(6-Acetyl-3,4-dihydro-3-hydroxy-2,2-dimethyl-2H-1benzopyran-4-yl)-3-phenylurea A suspension of the title C compound (0.1 g, 0.42 mmol) in dichloromethane (5 ml) under argon was treated with triethyl amine (0.04 g, 0.42 mmol) followed by phenyl isocyanate (0.05 g, 0.42 mmol). The reaction was stirred at room temperature for 4 hours. The product precipitated out of the reaction mixture. It was filtered and washed with dichloromethane to yield the title compound (0.15 g), m.p. 210-211° C. $^1$H NMR (DMSO) δ 8.6 (s, 1 H), 7.82 (m, 3 H), 7.44 (d, J=9.0 Hz, 2 H), 7.25 (m, 2 H), 6.95 (m, 1 H), 6.86 (d, J=9.0 Hz, 1 H), 6.55 (d, J=9.0 Hz, 1 H), 5.6 (d, J=8.0 Hz, 1 H), 4.7 (m, 1 H), 3.5 (m, 1 H), 3.4 (m, 1 H), 2.4 (s, 3 H), 1.4 (s, 3 H), 1.2 (s, 3 H); IR (KBr) 3340.9, 2980.2, 1653.1, 1601.0, 1550.9, 1498.8, 1442.8, 1357.9, 1371.5, 1271.2, 1130.4 cm$^{-1}$.

Analysis calc'd for $C_{20}H_{22}N_2O_4 \cdot 0.44 H_2O$:

C, 66.31; H, 6.36; N, 7.73; Found: C, 66.28; H, 6.08; N, 7.76.

EXAMPLE 13

(trans)-3,4-Dihydro-3-hydroxy-2,2-dimethyl-4(2,3-dihydro-2-oxo-1H-benzimidazol-1-yl)-2H-1-benzopyran-6-carbonitrile

A. N-(Ethoxycarbonyl)-2-nitroaniline

To a solution of 2-nitroaniline (6.9 g, 50.0 mmol) in pyridine (6 mL) and dichloromethane (25 mL) at 0° C. under argon was added ethylchloroformate (7.3 mL, 75.0 mmol) through an addition funnel. After the addition was finished, the cooling bath was removed and the reaction mixture was allowed to stir at room temperature overnight. The reaction mixture was poured into 2N hydrochloric acid and extracted with ethyl acetate. The combined extracts were washed with water, saturated sodium bicarbonate solution and brine. After drying over anhydrous magnesium sulfate, the solvent was evaporated to yield the title A compound as a yellow solid (7.7 g). $^1$H NMR (CDCl$_3$) δ 8.55 (d, J=8.0 Hz, 1 H), 8.2 (d, J=8.0 Hz, 1 H), 7.6 (t, J=8.0 Hz, 1 H), 7.1 (t, J=7.5 Hz, 1 H), 4.25 (q, J=6.0 Hz, 2 H), 1.3 (t, J=6.0 Hz, 3 H); $^{13}$C NMR (CDCl$_3$) 153.0, 135.8, 135.4, 125.7, 122.1, 120.5, 63.6, 14.3 ppm.

B. 2-[(Ethoxycarbonyl)amino]aniline

The solution of the title A compound (2.0 g, 9.5 mmol) in absolute ethanol (25 mL) was hydrogenated at atmospheric pressure in the presence of 10% palladium hydroxide/carbon catalyst (200 mg). The catalyst was filtered off using a celite pad and the filtrate was evaporated. The residue was crystallized from isopropyl ether to give the title B compound as a colorless solid (820 mg). $^1$H NMR (CDCl$_3$) δ 7.2 (d, J=7.0 Hz, 1 H), 7.0 (t, J=6.5 Hz, 1 H), 6.7 (m, 3 H), 4.2 (q, J=6.0 Hz, 2 H), 3.75 (br s, 2 H), 1.3 (t, J=6.0 Hz, 3 H); $^{13}$C NMR (CDCl$_3$) 158.2, 140.0, 126.3, 124.9, 124.0, 119.3, 117.3, 61.3, 14.4 ppm.

C.

(trans)-3,4-Dihydro-3-hydroxy-2,2-dimethyl-4[2-[((ethoxycarbonyl)amino)phenyl]amino]-2H-1-benzopyran-6-carbonitrile The reaction mixture containing the title B compound (900 mg, 5.0 mmol), 6-cyano-3,4-dihydro-2,2-dimethyl-3,4-epoxy-2H-1-benzopyran (1.0 g, 5.0 mmol, prepared according to Evans et al., *J. Med. Chem.*, 1983, 26, p. 1582 and *J. Med. Chem.*, 1986, 29, p. 2194) and magnesium perchlorate (1.12 g, 5.0 mmol) in acetonitrile (5.0 mL) was stirred under argon at room temperature for 48 hours. The reaction mixture was diluted with ethyl acetate and washed with water, saturated sodium bicarbonate solution and brine. After drying over anhydrous magnesium sulfate, the solvent was evaporated to give the title C compound as a colorless foam (2.02 g). $^1$H NMR (CDCl$_3$) δ 7.57 (s, 1 H), 7.30 (dd, J=8.8 and 2.3 Hz, 1 H), 7.0 (m, 2 H), 6.75 (d, J=8.2 Hz, 2 H), 6.60 (m, 3 H), 4.3 (m, 2 H), 4.05 (m, 3 H), 3.60 (d, J=8.8 Hz, 1 H), 1.4 (s, 3 H), 1.2 (s, 3 H), 1.16 (t, J=7.0 Hz, 3 H); $^{13}$C NMR (CDCl$_3$) 156.5, 155.9, 142.9, 132.6, 128.0, 127.3, 126.5, 124.9, 122.8, 119.2, 118.2, 118.0, 113.5, 103.5, 80.0, 72.5, 61.88, 54.7, 26.7, 19.2, 14.3 ppm.

D.

(trans)-3,4-Dihydro-3-hydroxy-2,2-dimethyl-4(2,3-dihydro-2-oxo-1H-benzimidazol-1-yl)-2H-1-benzopyran-6-carbonitrile To the solution of the title C compound 1.15 g, 3.02 mmoles) in methanol (6.0 mL) was added sodium methoxide-methanol solution (1.04 mL of 4.4M solution, 9.0 mmol) and the reaction mixture was refluxed under argon for 4 hours. More sodium methoxide solution (1.04 mL) was added and the heating was continued for 4 additional hours. The reaction mixture was cooled to ambient temperature and diluted with ethyl acetate. It was washed with citric acid, saturated sodium bicarbonate solution and brine. After drying over anhydrous magnesium sulfate, the solvent was evaporated and the residue was purified by flash chromatography (20% acetone in dichloromethane). The resulting product was crystallized from isopropyl alcohol in two crops to yield the title compound (605 mg), m.p. 255-257° C. IR(KBr) 2225, 1682, 1491 cm$^{-1}$; $^1$H NMR (DMSO-d$_6$) δ 7.60 (dd, J=8.4 and 1.8 Hz, 1 H), 7.55, 7.38 (d, J=8.8 Hz, 1 H), 7.18 (s, 1 H), 7.06 (m, 2 H), 6.95 (t, J=8.1 Hz, 1 H), 6.77 (t, J=7.6 Hz, 1 H), 6.16 (d, J=7.7 Hz, 1 H), 5.91 (d, J=6.3 Hz, 1 H), 5.41, 5.13, (d, J=10.0 Hz, 1 H), 4.45, 4.07 (dd, J=9.5 and 5.8 Hz, 1 H), 1.45, 1.43 (s, 3 H), 1.27, 1.25 (s, 3 H). The NMR shows doubling of signals due to two rotamers present in solution.

Analysis calc'd for C$_{19}$H$_{17}$N$_3$O$_3$:
C, 68.05; H, 5.11; N, 12.53; Found: C, 67.95; H, 5.05; N, 12.37.

EXAMPLE 14

(trans)-1-(6-Cyano-3,4-dihydro-3-hydroxy-2,2-dimethyl-2H-1-benzopyran-4-yl)-(3-pyridinyl)urea A. 4-Nitrophenyl-(3-pyridinyl) carbamate A solution of 3-aminopyridine (5.0 g, 5.3 mmol) in methylene chloride (40 ml) was treated with a solution of 4-nitrophenylchloroformate (10.7 g, 5.3 mmol) in methylene chloride (40 ml) followed by pyridine (4.2 g, 5.3 mmol) under argon and the reaction mixture was allowed to stir at room temperature for 24 hours. The solid was filtered and washed with methylene chloride to give the title A compound (13.0 g) as a light yellow solid. $^1$H NMR (DMSO) δ 8.14 (d, J=7.1 Hz, 2 H), 8.02 (d, J=1.8 Hz, 1 H), 7.9 (m, 1 H), 7.5 (m, 2 H), 6.98 (d, J=7.0 Hz, 2 H).

B.

(trans)-1-(6-Cyano-3,4-dihydro-3-hydroxy-2,2-dimethyl-2H-1-benzopyran-4-yl)-(3-pyridinyl)urea A solution of (trans)-4-amino-3,4-dihydro-3-hydroxy-2,2-dimethyl-2H-1-benzopyran-6-carbonitrile (1.0 g, 4.6 mmol, prepared according to Evans et al., *J. Med. Chem.*, 1983, 26, p. 1582 and *J. Med. Chem.*, 1986, 29, p. 2194) in acetonitrile (20 ml) under argon was treated with the title A compound (1.8 g, 6.9 mmol) and the reaction was heated at 80° C. for 4 hours. The solid was filtered off and the filtrate was concentrated in vacuo. The residue was diluted with ethyl acetate and washed with water (3×200 ml), saturated sodium bicarbonate solution, water and concentrated in vacuo. This residue was triturated with ethyl acetate to give the title compound (1.4 g) as a colorless solid, m.p. 225-227° C. $^1$H NMR (DMSO) δ 9.0 (s, 1 H), 8.42 (d, J=4.7 Hz, 1 H), 8.25 (d, J=8.2 Hz, 1 H), 7.80 (m, 1 H), 7.79 (m, 2 H), 7.38 (d, J=8.8 Hz, 1 H), 6.95 (d, J=8.8 Hz, 1 H), 4.74 (t, J=8.8 Hz, 1 H), 3.65 (d, J=9.4 Hz, 1 H), 1.44 (s, 3 H), 1.21 (s, 3 H); $^{13}$C NMR (DMSO) 156.3, 155.3, 139.5, 135.8, 132.6, 132.3, 130.8, 126.4, 125.5, 119.1, 117.9, 102.7, 80.4, 71.2, 49.5, 26.5, 18.9; IR (KBr) 1265.4, 1369.5, 1487.2, 1548.9, 1610.7 1697.5, 2222.1, 1769.9, 2986.0, 3068.9, 3296.6 cm$^{-1}$.

Analysis calc'd for C$_{18}$H$_{18}$N$_4$O$_3$.1.53 H$_2$O:
C, 59.07: H. 5.80: N. 15.31: Found: C. 59.07: H. 6.12: N. 15.12.

EXAMPLE 15

(trans)-3,4-dihydro-3-hydroxy-2,2-dimethyl-4-(2-oxo-3-phenyl-1-imidazolidinyl)-2H-1-benzopyran-6-carbonitrile

A.

(trans)-3,4-dihydro-3-hydroxy-2,2-dimethyl-4-phenylethylenediamino-2H-1-benzopyran-6-carbonitrile A solution of 6-cyano-3,4-dihydro-2,2-dimethyl-3,4-epoxy-2H-1-benzopyran (1.0 g, 5.0 mmol, prepared according to Evans et al., *J. Med. Chem.*, 1983, 26, p. 1582 and *J. Med. Chem.*, 1986, 29, p. 2194) in ethanol (10 ml) was treated with phenylethylenediamine (0.74 g, 5.4 mmol) under argon and allowed to stir at room temperature for 24 hours. The reaction mixture was concentrated in vacuo to give the title A compound (1.5 g) as a colorless solid.

B.

(trans)-3,4-dihydro-3-hydroxy-2,2-dimethyl-4-(2-oxo-3-phenyl-1-imidazolidinyl)-2H-1-benzopyran-6-carbonitrile A solution of the title A compound (1.67 g, 5.0 mmol) in methylenechloride (20 ml) under argon at 0° C. was treated with a solution of 4-nitrophenylchloroformate (1.3 g, 6.4 mmol) in methylene chloride (10 ml) followed by triethylamine (0.65 g, 6.4 mmol). The reaction was allowed to stir at room temperature for 16 hours. It was then diluted with methylene chloride and washed with 10% hydrogen chloride solution and water. The organic layer was dried over anhydrous magnesium sulfate and concentrated in vacuo to give the crude product which was recrystallized from a mixture of ether and ethyl acetate to give the title compound (0.7 g) as a colorless solid, m.p. 205–206° C. $^1$H NMR (CDCl$_3$) δ 7.52 (m, 7 H), 7.24 (t, J=7.6 Hz, 1 H), 7.02 (d, J=8.7 Hz, 1 H), 5.30 (d, J=10.5 Hz, 1 H), 3.88 (d, J=5.8 Hz, 1 H), 3.87 (m, H), 3.57 (m, 1 H), 3.27 (m, 1 H), 1.71 (s, 3 H), 1.45 (s, 3 H); $^{13}$C NMR (DMSO) 159.0, 157.5, 139.6, 133.1, 131.8, 128.8, 123.0, 120.9, 119.0, 118.7, 117.7, 104.0, 80.4, 69.7, 52.7, 42.5, 36.8, 26.7, 18.5; IR (KBr) 1269.2, 1429.3, 1487.2 1599.1, 1684.0, 2224.1, 2895.3, 2978.3, 3445.1 cm$^{-1}$.

Analysis calc'd for C$_{21}$H$_{21}$N$_3$O$_3$:

C, 69.40; H. 5.83: N. 11.56; Found: C, 69.08; H, 5.70; N, 11.54.

EXAMPLE 16

(cis)-1-(6-Cyano-3,4-dihydro-3-hydroxy-2,2-dimethyl-2H-1-benzopyran-4-yl)-3-phenylurea

A.

(trans)-4-Acetylamino-8-cyano-3,4-dihydro-2,2-dimethyl-3-hydroxy-2H-1-benzopyran To a solution of (trans)-4-amino-6-cyano-3,4-dihydro-2,2-dimethyl-3-hydroxy-2H-1-benzopyran (3.0 g, 13.8 mmoles, prepared according to Evans et al., *J. Med. Chem.*, 1983, 26, p. 1582 and *J. Med. Chem.* 1986, 29, p. 2194) in 20% water/tetrahydrofuran (40 ml) was added simultaneously (dropwise) acetyl chloride (1.66 g, 21.1 mmoles) and 20% aqueous sodium bicarbonate solution with rapid stirring. The pH was maintained at ≧9.0. The reaction mixture was stirred an additional 15 minutes at room temperature and evaporated in vacuo. The residue was partitioned between ethyl acetate and 5% aqueous hydrogen chloride solution. The organic layer was washed with saturated sodium hydrogen carbonate solution, saturated sodium chloride solution and dried over anhydrous magnesium sulfate. The solvent was recovered to obtain 3.30 g of the title A compound as a white solid. $^1$H NMR (DMSO-d$_6$) δ 8.28 (d, J=8.80 Hz, 1 H), 7.59 (d, J=9.97 Hz, 1 H), 7.49 (s, 1 H), 6.92 (d, J=8.21 Hz, 1 H), 4.82 (t, J=8.80 Hz, 1 H), 3.55 (dd, J=5.57 and 9.68 Hz, 1 H), 1.99 (s, 3 H), 1.42 (s, 3 H), 1.18 (s, 3 H). $^{13}$C NMR (DMSO-d$_6$) δ 170.50, 156.27, 132.74, 132.57, 125.28, 119.06, 117.88, 102.80, 80.22, 71.23, 48.54, 38.58, 26.54, 22.94.

B.

(cis)-4-Acetylamino-6-cyano-3,4-dihydro-2,2-dimethyl-3-hydroxy-2H-1-benzopyran

To a solution of the title A compound (3.25 g, 12.5 mmoles) in dichloromethane (30 ml) under argon was added diethylaminosulfur trifluoride (2.21 g, 13.7 mmoles, 1.1 eq.) at room temperature. The reaction mixture was stirred 18 hours, the solvent was recovered under vacuum. The residue was partitioned between ethyl acetate and saturated sodium hydrogen carbonate. The organic layer was washed with saturated sodium chloride solution, dried over anhydrous mangesium sulfate and evaporated in vacuo to obtain 3.02 g of colorless gum. The crude oxazoline was dissolved in dioxane (30 ml), treated with 0.25N aqueous sulfuric acid (1 ml) and stirred 18 hours at room temperature. The reaction mixture was partitioned between ethyl acetate and distilled water. The organic phase was washed with saturated sodium hydrogen carbonate solution, saturated sodium chloride solution, dried over magnesium sulfate and evaporated in vacuo to obtain 2.53 g of crude cis-amido alcohol. The crude product was chromatographed on silica eluting with ethyl acetate to obtain 1.08 g of the title B compound as a white solid. $^1$H NMR (DMSO-d$_6$) δ 8.12 (d, J=8.79 Hz, 1 H), 7.58 (d, J=8.21 Hz, 1 H), 7.48 (s, 1 H), 6.88 (d, J=8.21 Hz, 1 H), 5.67 (d, J=5.27 Hz, 1 H), 5.20 (d, J=5.87 Hz, 1 H), 3.60 (m, 1 H), 2.02 (s, 3 H), 1.39 (s, 3 H), 1.25 (s, 3 H). $^{13}$C NMR (DMSO-d$_6$) δ 170.12, 157.29, 132.51, 132.25, 122.75, 119.32, 117.42, 101.93, 79.58, 67.66, 45.17, 24.90, 24.04, 22.65.

C.

(cis)-4-Amino-6-cyano-3,4-dihydro-2,2-dimethyl-3-hydroxy-2H-1-benzopyran

A solution of the title B compound (0.80 g, 3.1 mmoles) in dioxane (9 ml) and 1.5M aqueous sulfuric acid (6.4 ml) was heated at 75° C. for 48 hours. The reaction mixture was concentrated under vacuum and partitioned between 2N sodium hydroxide and ethyl acetate. The organic layer was washed with saturated sodium chloride solution, dried over sodium sulfate and evaporated in vacuo to obtain 0.65 g of an off-white solid. The crude amino alcohol was chromatographed on silica eluting with 5% methanol in ethyl acetate to obtain 0.54 g of the title C compound as a pure white solid. $^1$H NMR (DMSO-d$_6$) δ 8.00 (s, 1 H), 7.52 (d, J=8.79 Hz, 1 H), 6.80 (d, J=8.21 Hz, 1 H), 5.31 (broad s, 1 H), 3.92 (d, J=3.52 Hz, 1 H), 3.50 (broad s, 1 H), 3.33 (broad s, 1 H), 1.38 (s, 3 H), 1.20 (s, 3 H). $^{13}$C NMR (DMSO-d$_6$) δ 156.93, 133.06, 131.56, 127.36, 119.61, 116.85, 101.61, 79.41, 70.43, 46.64, 25.07, 24.32.

D.

(cis)-1-(6-Cyano-3,4-dihydro-3-hydroxy-2,2-dimethyl-2H-1-benzopyran-4-yl)-3-phenylurea A solution of the title C compound (0.18 g, 0.80 mmoles) and phenyl isocyanate (0.10 g, 0.84 mmoles, 1.05 eq.) in ethanol (2 ml) was heated at reflux for 3 hours. The ethanol was recovered under vacuum and the residue was triturated with isopropyl ether to obtain 0.26 g of the title compound as a white solid, m.p. 226–227° C. $^1$H NMR (DMSO-d$_6$) δ 8.89 (s, 1 H), 7.58 (d, J=8.20 Hz, 1 H), 7.54 (s, 1 H), 7.45 (d, J=7.62 Hz, 2 H), 7.26 (m, 2 H), 6.92 (m, 2 H), 6.58 (d, J=8.79 Hz, 1 H), 5.84 (d, J=5.86 Hz, 1 H), 5.08 (m, 1 H), 3.66 (m, 1 H), 1.41 (s, 3 H), 1.28 (s, 3 H).

Analysis calc'd for C$_{19}$H$_{19}$N$_3$O$_3$.0.26 H$_2$O:

C, 66.71; H, 5.75; N, 12.28; Found: C, 66.90; H, 5.77; N, 12.09.

EXAMPLE 17

(trans)-N-[3,4-Dihydro-3-hydroxy-2,2-dimethyl-6-(trifluoromethyl)-2H-1-benzopyran-4-yl]-N'-phenylurea A suspension of (trans)-4-amino-3,4-dihydro-3-hydroxy-2,2-dimethyl-6-trifluoromethyl-2H-1-benzopyran (0.5 g, 1.9 mmol) (prepared according to D. R. Buckle et al., *J. Med. Chem.*, 1990, 33, p. 3028) in ethanol (5 ml) under argon was treated with phenylisocyanate (0.23 g, 1.9 mmol) and the reaction was heated at reflux temperature for 4 hours. The product precipitated out of the reaction. The reaction was then concentrated in vacuo and the residue was triturated with isopropyl ether and hexanes to give the title compound as a colorless solid (0.5 g), m.p. 174–175° C.: $^1$H NMR (CDCl$_3$) δ 7.4 (s, 1 H), 7.32 (d, J=9.8 Hz, 1 H), 7.17 (m, 5 H), 7.0 (m, 1 H), 6.77 (d, J=8.2 Hz, 1 H), 5.22 (br d, 1H), 4.80 (br t, 1 H), 3.45 (d, J=9.4 Hz, 1 H), 1.37 (s, 3 H), 1.12 (s, 3 H); $^{13}$C NMR (CDCl$_3$) 157.0, 156.5, 139.1, 137.3, 129.4, 126.5, 125.0, 124.7, 122.0, 121.7, 118.0, 79.6, 76.4, 51.4, 26.3, 18.2; IR (KBr) 1118.5, 1264.8, 1332.1, 1443.4, 1500.9, 1558.3, 1598.8, 1647.8, 2981.4, 3391.3 cm$^{-1}$.

Analysis calc'd for $C_{19}H_{19}F_3N_2O_3$:
C. 59.99: H. 5.03: N. 7.37: F. 14.99: Found: C 59.78: H. 5.08: N, 7.39: F. 15.13.

EXAMPLE 18

(trans)-1-(6-Cyano-3,4-dihydro-3-hydroxy-2,2-dimethyl-2H-1-benzopyran-4-yl)-(2-pyridinyl)urea

A. 4-Nitrophenyl-(2-pyridinyl)carbamate

A solution of 2-aminopyridine (2.0 g, 21.3 mmol) in methylene chloride (20 ml) was treated with a solution of 4-nitrophenylchloroformate (4.3 g, 21.3 mmol) in methylene chloride (30 ml) followed by the addition of pyridine (1.7 g, 21.3 mmol) under argon. The reaction mixture was allowed to stir at room temperature for 24 hours. The solid was filtered and washed with methylene chloride to give the title A compound (4.8 g) as a light yellow solid.

B. (trans)-1-(6-Cyano-3,4-dihydro-3-hydroxy-2,2-dimethyl-2H-1-benzopyran-4-yl)-(2-pyridinyl)urea A solution of (trans)-4-amino-3,4-dihydro-3-hydroxy-2,2-dimethyl-2H-1-benzopyran-6-carbonitrile (prepared according to Evans et al., *J. Med. Chem.*, 1983, 26, p. 1582 and *J. Med. Chem.*, 1986, 29, p. 2194) (1.0 g, 4.6 mmol) in dimethylformamide (10 ml) under argon was treated with the title A compound (1.8 g, 6.9 mmol) and the reaction was heated at 80° C. for 4 hours. The reaction mixture was concentrated in vacuo and the residue was diluted with ethyl acetate. It was washed with water (3×200 ml), saturated sodium bicarbonate solution, water and concentrated in vacuo. The residue was crystallized from ether-hexanes to give a solid (0.84 g). This solid was recrystallized from isopropyl ether-dichloromethane to give the title compound as a colorless solid (0.5 g), m.p. 192-194° C.: $^1$H NMR (CDCl$_3$) δ 9.2 (s, 1 H), 8.17 (d, J=4.1 Hz, 1 H), 7.83 (s, 1 H), 7.71 (t, J=6.5 Hz, 1 H), 7.57 (d, J=8.8 Hz, 1 H), 6.99 (m, 3 H), 5.20 (t, J=8.2 Hz, 1 H), 5.0 (s, 1 H), 3.91 (d, J=8.8 Hz, 1 H), 1.64 (s, 3 H), 1.42 (s, 3 H); $^{13}$C NMR (CDCl$_3$) 158.4, 156.9, 152.6, 146.0, 138.8, 133.1, 132.3, 123.1, 119.0, 118.6, 117.7, 112.2, 104.1, 80.2, 75.7, 51.2, 26.4, 18.7; IR (KBr) 1268.2, 1305.5, 1489.9, 1556.1, 1584.2, 1679.1, 2224.8, 2979.7, 3063.6, 3411.1 cm$^{-1}$.

Analysis calc'd for $C_{18}H_{18}N_4O_3.0.66 H_2O$:
C, 63.47; H, 5.40; N, 16.45; Found: C, 63.37; H, 5.31; N, 16.55.

EXAMPLE 19

(trans)-1-(6-Cyano-3,4-dihydro-3-hydroxy-2,2-dimethyl-2H-1-benzopyran-4-yl)-(4-pyridinyl)urea

A. 4-Nitrophenyl-(4-pyridinyl) carbamate

To a solution of 4-aminopyridine (2.0 g, 21.3 mmol) in methylene chloride (20 ml) was added a solution of 4-nitrophenylchloroformate (4.3 g, 21.3 mmol) in methylene chloride (30 ml) followed by the addition of pyridine (1.7 g, 21.3 mmol) under argon. The reaction mixture was allowed to stir at room temperature for 24 hours. The solid was filtered and washed with methylene chloride to give the title A compound (5.0 g) as a light yellow solid.

B. (trans)-1-(6-Cyano-3,4-dihydro-3-hydroxy-2,2-dimethyl-2H-1-benzopyran-4-yl)-(4-pyridinyl)urea A solution of (trans)-4-amino-3,4-dihydro-3-hydroxy-2,2-dimethyl-2H-1-benzopyran-6-carbonitrile (1.0 g, 4.6 mmol) (prepared according to Evans et al., *J. Med. Chem.*, 1983, 26, p. 1582 and *J. Med. Chem.*, 1986, 29. p. 2194) in dimethylformamide (10 ml) under argon was treated with the title A compound (1.8 g, 6.9 mmol) and the reaction was heated at 80° C. for 16 hours. The reaction mixture was concentrated in vacuo and the residue was diluted with ethyl acetate. It was washed with water (3×200 ml), saturated sodium bicarbonate solution, water and concentrated in vacuo. The residue was flash chromatographed on silica gel eluting with acetone/ethyl acetate (1:1) to yield a solid (0.21 g). This solid was triturated with ethyl acetate to give the title compound (0.18 g) as a colorless solid, m.p. 227-228° C.: $^1$H NMR (CDCl$_3$) δ 8.73 (s, 1 H), 8.30 (d, J=5.9 Hz, 2 H), 7.58 (s, 1 H), 7.35 (m, 3 H), 6.79 (d, J=9.8 Hz, 1 H), 6.52 (d, J=7.7 Hz, 1 H), 5.29 (s, 1 H), 4.80 (t, J=9.4 Hz, 1 H), 3.53 (d, J=10.0 Hz, 1 H), 1.44 (s, 3 H), 1.22 (s, 3 H); $^{13}$C NMR (CDCl$_3$) 156.0, 155.7, 149.6, 146.5, 132.1, 124.1, 117.7, 102.9, 79.9, 73.0, 49.6, 26.0, 18.3; IR (KBr) 1267.0, 1334.0, 1490.6, 1532.8, 1594.3, 1699.5, 2226.9, 2979.9, 3365.4 cm$^{-1}$.

Analysis calc'd for $C_{18}H_{18}N_4O_3.0.72 H_2O$:
C, 61.53; H, 5.58; N, 15.94; Found: C, 61.94; H, 5.15; N, 15.53.

EXAMPLE 20

(−)-N-(6-Cyano-3,4-dihydro-2,2-dimethyl-2H-1-benzopyran-4-yl-N'-(phenylmethyl)urea

A. N-(6-Cyano-3,4-dihydro-2,2-dimethyl-2H-1-benzopyran-4-yl)-α-hydroxybenzeneacetamide To a solution of R-(−)-mandelic acid (22.1 g, 0.14 mole) and 1-hydroxybenzotriazole hydrate (19.6 g, 0.14 mole) cooled to 0° C. was added successively N-methylmorpholine (16.2 g, 0.16 mole), 4-amino-6-cyano-3,4-dihydro-2,2-dimethyl-2H-1-benzopyran (29.4 g, 0.14 mole, Example 8, part D) and 1-(3-dimethylaminopropyl)-2-ethylcarbodiimide.HCl (27.9 g, 0.14 mole). The reaction mixture was stirred 0.5 hours at 0° C. and two hours at room temperature. The solvent was recovered under vacuum and the residue was partitioned between 5% aqueous HCl and ethyl acetate. The organic fraction was washed with saturated sodium bicarbonate solution, saturated sodium chloride solution, dried over magnesium sulfate and evaporated in vacuo to obtain 52 g of yellow gum. The crude diastereomer mixture was chromatographed on silica eluting with 1:1 hexane/ethyl acetate to obtain 23.2 g (47.7%) of Isomer A. m.p.=120-121° C., $[α]^D_{25}=-39.5°$. $^1$H NMR (CDCl$_3$) δ 7.43-7.34 (m, 7H), 6.81 (d, J=8.20 Hz, 2H), 5.23 (m, 1H), 5.13 (d, J=3.52 Hz, 1H), 4.27 (m, 1H), 2.08 (dd, J=5.86 and 13.78 Hz, 1H), 1.71 (d, J=12.31 Hz, 1H), 1.42 (s, 3H), 1.36 (s, 3H). $^{13}$C NMR (CDCl$_3$) δ 173.26, 158.09, 139.60, 133.30, 132.46, 129.27, 129.18, 126.88, 123.39, 119.62, 118.99, 103.64, 77.00, 74.50, 42.33, 39.59, 29.77, 25.05. MS: (M+H)+@337.

B.
(−)-4-Amino-6-cyano-3,4-dihydroxy-2,2-dimethyl-2H-1-benzopyran

A solution of N-(6-cyano-3,4-dihydro-2,2-dimethyl-2H-1-benzopyran-4-yl)-α-hydroxybenzeneacetamide (22.3 g, 66.2 mmole-Isomer A, from Example 19, part A) in a mixture of dioxane (195 ml) and 1.5M $H_2SO_4$ (140 ml) was heated at 75-85° C. for five days. The reaction mixture was concentrated under vacuum and the concentrate was partitioned between distilled water and ethyl acetate. The aqueous phase was washed with ethyl acetate, made basic (pH>12) with 50% NaOH solution and extracted with diethyl ether. The ether extracts were washed with saturated NaCl solution, dried over $Na_2SO_4$ and evaporated in vacuo to obtain 9.58 g (72%) of the title compound as a yellow oil which crystallized on standing. $[α]^D_{25}$ $CHCl_3$= −95.8°. $^1$H NMR ($CDCl_3$) δ 7.86 (s, 1H), 7.40 (dd, J=2.35 and 8.80 Hz, 1H), 6.80 (d, J=8.20 Hz, 1H), 4.02 (dd, J=5.86 and 11.14 Hz, 1H), 2.13 (dd, J=5.87 and 13.49 Hz, 1H), 1.66 (d, J=11.73 Hz, 1H), 1.46 (s, 3H), 1.30 (s, 3H). $^{13}$C NMR ($CDCl_3$) δ 157.14, 132.09, 132.00, 127.48, 119.50, 118.01, 102.97, 76.83, 44.06, 43.77, 29.63, 24.94.

C.
(−)-N-(6-Cyano-3.4-dihydro-2,2-dimethyl-2H-1-benzopyran-4-yl-N′-(phenylmethyl)urea A solution of (−)-4-amino-6-cyano-3,4-dihydro-2,2-dimethyl-2H-1-benzopyran (2.0 g, 9.9 mmole, from Example 19, part B) and benzyl isocyanate (1.32 g, 9.9 mmole) in ethanol (15 ml) under argon was heated at reflux for two hours. The solvent ws recovered under vacuum and the crude product was triturated with isopropyl ether to obtain 2.98 g (89.7%) of the title compound as a pure white solid. m.p.=140-141° C., $[α]^D_{25}$ DMF=−41.2°. $^1$H NMR (DMSO-$d_6$) δ 7.59 (s, 1H), 7.56 (d. J=1.76 Hz, 1H), 7.38-7.22 (m, 5H), 6.89 (d, J=8.21 Hz, 1H), 6.56 (t, J=5.87 Hz, 1H), 6.49 (d, J=8.79 Hz, 1H), 4.94 (m, 1H), 4.30 (d, J=5.87 Hz, 1H), 2.11(dd, J=6.16 and 13.19 Hz, 1H), 1.74 (d, J=12.32 Hz, 1H), 1.41 (s. 3H), 1.28 (s, 3H). $^{13}$C NMR (DMSO-d) δ 158.19, 157.27, 140.80, 132.25, 132.15, 128.31, 126.98, 126.69, 126.18, 119.28, 118.13, 102.06., 77.37, 43.08, 42.01, 37.80, 29.15, 24.47. MS: (M+H)+@336.

Analysis calculated for $C_{20}H_{21}N_3O_2$:
C, 71.62; H, 6.31; N, 12.53; Found: C, 71.60; H, 6.28; N, 12.21.

EXAMPLE 21
(+)-N-(6-Cyano-3.4-dihydro-2,2-dimethyl-2H-1-benzopyran-4-yl-N′-(phenylmethyl)urea

A.
N-(6-Cyano-3,4-dihydro-2,2-dimethyl-2H-1-benzopyran-4-yl)-α-hydroxybenzeneacetamide To a solution of R-(−)-mandelic acid (22.1 g, 0.14 mole) and 1-hydroxy-benzotriazole hydrate (19.6 g, 0.14 mole) cooled to 0° C. was added successively N-methylmorpholine (16.2 g, 0.16 mole), 4-amino-6-cyano-3,4-dihydro-2,2-dimethyl-2H-1-benzopyran (29.4g, 0.14 mole, from Example 8, part D) and 1-(3-dimethylaminopropyl)-2-ethylcarbodiimide.HCl (27.9 g, 0.14 mole). The reaction mixture was stirred 0.5 hours at 0° C. and two hours at room temperature. The solvent was recovered under vacuum and the residue was partitioned between 5% aqueous HCl and ethyl acetate. The organic fraction was washed with saturated sodium bicarbonate solution, saturated sodium chloride solution, dried over magnesium sulfate and evaporated in vacuo to obtain 52 g of yellow gum. The crude diastereomer mixture was chromatographed on silica eluting with 1:1 hexane/ethyl acetate to obtain 19.8 g (40.6%) of Isomer B (isomer A being subject of Example 19, part A); m.p.=135-136° C., $[α]^D_{25}$=−60.8°. $^1$H NMR ($CDCl_3$) δ 7.51-7.30 (m, 6H), 7.27 (d, J=1.76 Hz, 1H), 6.80 (m, 2H), 5.18 (m, 1H), 5.08 (d, J=2.93 Hz, 1H), 3.97 (d, J=2.93 Hz, 1H), 2.12 (dd, J=6.15 and 13.19 Hz, 1H), 1.69 (dd, J=11.43 and 13.20 Hz, 1H), 1.40 (s, 3H), 1.30 (s, 3H); $^{13}$C NMR ($CDCl_3$) δ 172.59, 157.53, 139.13, 133.07, 132.81, 131.98, 128.92, 126.38, 122.86, 118.97, 118.56, 103.25, 76.83, 74.26, 41.81, 38.96, 29.15, 24.62; MS: (M+H)+@337.

B.
(+)-4-Amino-6-cyano-3,4-dihydroxy-2,2-dimethyl-2H-1-benzopyran

A solution of N-(6-cyano-3,4-dihydro-2,2-dimethyl-2H-1-benzopyran-4-yl)-a-hydroxybenzeneacetamide (18.8 g, 55.9 mmole-Isomer B, from Example 20, part A) in a mixture of dioxane (163 ml) and 1.5M $H_2SO_4$ (116 ml) was heated at 75-85° C. for five days. The reaction mixture was concentrated under vacuum and the concentrate was partitioned between distilled water and ethyl acetate. The aqueous phase was washed with ethyl acetate, made basic (pH>12) with 50% NaOH solution and extracted with diethyl ether. The ether extracts were washed with saturated brine solution, dried over sodium sulfate and evaporated in vacuo to obtain 8.90 g (72%) of the title compound as a yellow oil which crystallized on standing. $[α]^D_{25}$ $CHCl_3$=+95.4°. $^1$H NMR ($CDCl_3$) δ 7.86 (s, 1H), 7.40 (dd, J=2.35 and 8.80 Hz, 1H), 6.80 (d, J=8.20 Hz, 1H), 4.02 (dd, J=5.86 and 11.14 Hz, 1H), 2.13 (dd, J=5.87 and 13.49 Hz, 1H), 1.66 (d, J=11.73 Hz, 1H), 1.46 (s, 3H), 1.30 (s, 3H); $^{13}$C NMR ($CDCl_3$) δ 157.14, 132.09, 132.00, 127.48, 119.50, 118.01, 102.97, 76.83, 44.06, 43.77, 29.63, 24.94.

C.
(+)-N-(6-Cyano-3.4-dihydro-2,2-dimethyl-2H-1-benzopyran-4-yl-N′-(phenylmethyl)urea A solution of (+)-4-amino-6-cyano-3,4-dihydro-2,2-dimethyl-2H-1-benzopyran (2.0 g, 9.9 mmole, from Example 20, part B) and benzyl isocyanate (1.32 g, 9.9 mmole) in ethanol (15 ml) under argon was heated at reflux for two hours. The solvent ws recovered under vacuum and the crude product was triturated with isopropyl ether to obtain 2.79 g (84%) of the title compound as a pure white solid. m.p.=135-137° C., $[α]^D_{25}$DMF=+41.9°. $^1$H NMR (DMSO-$d_6$) δ 7.59 (s, 1H), 7.56 (d, J=1.76 Hz, 1H), 7.38-7.22 (m, 5H), 6.89 (d, J=8.21 Hz, 1H), 6.56 (t, J=5.87 Hz, 1H), 6.49 (d, J=8.79 Hz, 1H), 4.94 (m, 1H), 4.30 (d, J=5.87 Hz, 1H), 2.11(dd, J=6.16 and 13.19 Hz, 1H), 1.74 (d, J=12.32 Hz, 1H), 1.41 (s. 3H), 1.28 (s, 3H); $^{13}$C NMR (DMSO-d) δ 158.19, 157.27, 140.80, 132.25, 132.15, 128.31, 126.98, 126.69, 126.18, 119.28, 118.13, 102.06., 77.37, 43.08, 42.01, 37.80, 29.15, 24.47; MS: (M+H)+@336.

Analysis calculated for $C_{20}H_{21}N_3O_2$:
C. 71.62: H. 6.31: N. 12.53: Found: C, 71.67; H, 6.30; N, 12.32.

EXAMPLE 22

3,4-Dihydro-2,2-dimethyl-4-(2-oxo-3-phenyl-1-imidazolidinyl)-2H-1-benzopyran-6-carbonitrile

A.

N-(6-Cyano-2,2-dimethyl-3,4-dihydro-2H-1-benzopyran-4-yl)-N'-phenylethylenediamine A solution of 4-bromo-6-cyano-3,4-dihydro-2,2-dimethyl-2H-1-benzopyran (0.75 g, 2.82 mmole, from Example 8, part B) and N-phenylethylenediamine (8.84 g, 10 eq.) containing $NaHCO_3$ (2.40 g, 5 eq.) in N,N-dimethylformamide (15 ml) was stirred for 48 hours at room temperature. The reaction mixture was partitioned between ethyl acetate and distilled $H_2O$. The organic phase was washed with distilled $H_2O$, saturated NaCl solution, dried over $Na_2SO_4$ and evaporated in vacuo to obtain 3.71 g of an orange gum. The crude product was chromatographed on silica eluting with 3:2 hexane/ethyl acetate to obtain 0.36 g (40%) of the title compound as a colorless gum which solidified upon standing. $^1H$ NMR ($CDCl_3$) δ 7.91 (s. 1H), 7.38 (dd, J=2.34 and 8.79 Hz, 1H), 7.19 (m, 2H), 6.79 (d, J=8.21 Hz, 1H), 6.70 (m, 3H), 3.87 (dd, J=5.86 and 11.14 Hz, 1H), 3.26 (m, 2H), 3.10 (m, 1H), 2.86 (m, 1H), 2.20 (dd, J=5.87 and 12.90 Hz, 1H), 1.58 (d, J=12.30 Hz, 1H), 1.45 (s, 3H), 1.27 (s, 3H); $^{13}C$ NMR ($CDCl_3$) δ 157.63, 148.16, 132.40, 132.09, 129.21, 125.32, 119.56, 118.09, 117.52, 112.97, 102.89, 76.83, 49.24, 44.89, 44.00, 39.25, 29.69, 24.96; MS: (M+H)+@322.

B.

3,4-Dihydro-2,2-dimethyl-4-(2-oxo-3-phenyl-1-imidazolidinyl)-2H-1-benzopyran-6-carbonitrile To a solution of N-(6-cyano-2,2-dimethyl-3,4-dihydro-2H-1-benzopyran-4-yl)-N'-phenylethylenediamine (0.36 g, 1.12 mmole, from Example 21, part A) and triethylamine (0.12 g, 1.18 mmole) in methylene chloride (4 ml) cooled to 0° C. was added a solution of 4-nitrophenyl chloroformate (0.24 g, 1.18 mmole) dissolved in methylene chloride (3 ml). The reaction mixture was stirred at room temperature for four hours. The solvent was evaporated in vacuo and the residue was partitioned between ethyl acetate and 5% aqueous HCl solution. The organic phase was washed with 2N NaOH solution, saturated NaCl solution, dried over $MgSO_4$ and solvent evaporated to obtain 420 mg of an orange gum. The crude product was chromatographed on silica eluting with hexane/ethyl acetate (4:1) to obtain 0.30 g of the title compound as a pure white solid. m.p.=166-168° C. $^1H$ NMR (DMSO-$d_6$) δ7.61 (m,4H), 7.35 (m,2H), 7.03 (m,1H), 6.95 (d, J=8.21 Hz, 1H), 5.21 (dd, J=6.45 and 11.73 Hz, 1H), 3.88 (m, 2H), 3.36 (m 1H), 3.14 (m, 1H), 2.03 (m, 2H), 1.47 (s, 3H), 1.33 (s, 3H); $^{13}C$ NMR (DMSO-$d_6$) δ158.08, 157.13, 140.58, 132.86, 131.56, 128.63, 121.86, 121.63, 119.15, 118.52, 117.05, 102.54, 77.31, 44.68, 42.06, 36.56, 34.06, 29.36, 24.01; MS: (M+H)+@348.

Analysis calculated for $C_{21}H_{21}N_3O_2.0.2H_2O$:

C. 71.87; H. 6.14: N. 11.97; Found: C, 71.97; H, 6.04; N, 11.87.

EXAMPLE 23

3,4-Dihydro-2,2-dimethyl-4-[2-oxo-3-(phenylmethyl)-1-imidazolidinyl]-2H-1-benzopyran-6-carbonitrile

A.

N-(6-Cyano-2,2-dimethyl-3,4-dihydro-2H-1-benzopyran-4-yl)-N'-benzylethylenediamine A solution of 4-bromo-6-cyano-3,4-dihydro-2,2-dimethyl-2H-1-benzopyran (1.50 g, 5.64 mmole, from Example 8, part B) and N-benzylethylenediamine (8.48 g, 10 eq.) containing $NaHCO_3$ (4.80 g, 5 eq.) in N,N-dimethylformamide (30 ml) was stirred for 48 hours at room temperature. The reaction mixture was partitioned between ethyl acetate and distilled $H_2O$. The organic phase was washed with distilled $H_2O$, saturated NaCl solution, dried over $Na_2SO_4$ and evaporated in vacuo to obtain 4.10 g of an orange oil. The crude product was chromatographed on silica eluting with 9:1 methylene chloride/methanol (trace of $NH_4OH$) to obtain 0.91 g (48%) of the title compound as a colorless gum. $^1H$ NMR ($CDCl_3$) δ 8.00 (s, 1H). 7.49-7.34 (m, 6H), 6.88 (d, J=8.80 Hz, 1H), 3.93-3.82 (m, 3H), 3.03-2.80 (m, 5H), 2.25 (dd, J=5.57 and 13.20 Hz, 1H), 1.67 (m, 1H), 1.53 (s, 3H), 1.35 (s, 3H); $^{13}C$ NMR ($CDCl_3$) δ 157.66, 139.89, 132.52, 132.03, 128.43, 128.14, 127.05, 125.55, 119.65, 118.06, 102.89, 76.86, 53.73, 49.38, 49.01, 45.32, 39.25, 36.40, 29.72, 25.02; MS: (M+H)+@334.

B.

3,4-Dihydro-2,2-dimethyl-4-[2-oxo-3-(phenylmethyl)-1-imidazolidinyl]-2H-1-benzopyran-6-carbonitrile To a solution of N-(6-cyano-2,2-dimethyl-3,4-dihydro-2H-1-benzopyran-4-yl)-N'-benzylethylenediamine (0.91 g, 2.71 mmole, from Example 22, part A) and 4-nitrophenyl chloroformate (0.57 g, 2.85 mmole) in methylene chloride (22.5 ml) cooled to 0° C. was added pyridine (0.27 g, 3.39 mmole). The reaction mixture was stirred at room temperature for 24 hours, diluted with methylene chloride and washed with 5% aqueous HCl solution, 2N NaOH solution and saturated NaCl solution. The extract was dried over $MgSO_4$ and evaporated in vacuo to obtain 1.32 g of an orange gum. The crude product was chromatographed on silica eluting with hexane/ethyl acetate (3:2) to obtain 0.65 g (66%) of the title compound as a colorless amorphous solid, m.p.=45-48° C. $^1H$ NMR ($CDCl_3$) δ 7.51-7.39 (m, 7H), 6.93 (d, J=9.38 Hz, 1H), 5.43 (dd, J=7.03 and 11.14 Hz, 1H), 4.55 (m, 2H), 3.36-3.20 (m, 3H), 3.05 (m, 1H), 1.99 (m, 2H), 1.59 (s, 3H), 1.45 (S, 3H); $^{13}C$ NMR ($CDCl_3$) δ 160.77, 158.29, 136.70, 132.49, 131.66, 128.60, 128.03, 127.48, 121.38, 119.16, 118.61, 103.29, 76.94, 48.17, 45.15, 41.90, 37.26, 34.96, 34.67, 29.75, 24.01; MS: (M+H)+@362.

Analysis calculated for $C_{22}H_{23}N_3O_2.0.21H_2O$:

C, 72.35; H, 6.46; N, 11.50; Found: C, 72.55; H, 6.31; N, 11.30.

EXAMPLE 24

(3S-trans)-3-[[[(6-Cyano-3,4-dihydro-3-hydroxy-2,2-dimethyl-2H-1-benzopyran-4-yl)amino]carbonyl]amino]benzeneacetic acid, methyl ester

A. 3-Amino phenylacetic acid methylester hydrochloride

A suspension of 3-amino phenylacetic acid (5.0 g, 33 mmol) in methanol (50 ml) at 0° C. under argon was slowly treated with thionyl chloride (19.4 g, 165 mmol). After completion of addition, the reaction mixture was allowed to warm up to room temperature and stirred for 16 hours. The solvent was evaporated and the residue was triturated with ethyl ether to give 3-amino phenylacetic acid methylester hydrochloride (5.3 g, 96.8%) as a colorless solid. $^1$H NMR (CDCl$_3$) δ 10.6 (s, 2 H), 7.42 (m, 4 H), 3.68 (s, 3 H). 3.66 (s,2 H); $^{13}$C NMR (CDCl$_3$) 172.5, 137.3, 133.1, 131.2, 130.8, 125.9, 123.7, 53.5, 41.5.

B.

3[[[(4-nitrophenyl)oxy]-carbonyl]amino]benzeneacetic acid, methylester

To a suspension of 3-amino phenylacetic acid methylester hydrochloride (1.7 g, 10 mmol) in methylene chloride (30 ml) was added pyridine (0.79 g, 10 mmol) followed by the addition of a solution of 4-nitrophenylchloroformate (4.3 g, 21.3 mmol) in methylene chloride (30 ml) under argon. The reaction mixture was allowed to stir at room temperature for 24 hours. It was then washed with water (100 ml), 10% sodium hydroxide (100 ml), water (1100 ml) and dried over anydrous magnesium sulphate and concentrated in vacuo. The residue was triturated with isopropyl ether to give 3[[[(4-nitrophenyl)oxy]-carbonyl]amino]benzeneacetic acid, methylester (1.8 g, 53%) as a light yellow solid.

C.

(3S-trans)-3-[[[(6-Cyano-3,4-dihydro-3-hydroxy-2,2-dimethyl-2H-1-benzopyran-4-yl) amino]carbonyl]amino]-benzeneacetic acid, methyl ester A solution of (trans)-4-amino-3,4-dihydro-3-hydroxy-2,2-dimethyl-2H-1-benzopyran-6-carbonitrile (1.0 g, 4.6 mmol, prepared according to Evans et al., *J. Med. Chem.*, 1983, 26, p. 1582 and *J. Med. Chem.*, 1986, 29, p. 2194) in acetonitrile (30 ml) under argon was treated with 3[[[(4-nitrophenyl)oxy]carbonyl]-amino]benzeneacetic acid, methylester (1.7 g, 5.2 mmol) and the reaction was heated at 80° C. for 16 hours. The reaction mixture was concentrated in vacuo and the residue was diluted with ethyl acetate. It was washed with 10% hydrochloric acid (100 ml), water (100 ml) and concentrated in vacuo. The residue was flash chromatographed on silica gel eluting with acetone/methylene chloride (2:8) to give (3S-trans)-3-[[[(6-cyano-3,4-dihydro-3-hydroxy-2,2-dimethyl-2H-1-benzopyran-4-yl) amino]carbonyl]amino]benzeneacetic acid, methyl ester as a colorless solid (1.2 g, 63.9%), m.p. 72-75° C.: $^1$H NMR (DMSO-d$_6$) δ 8.82 (s, 1 H), 7.74 (m, 2 H), 7.55 (m, 2 H), 7.34 (m, 1 H), 7.08 (d, J=8.2 Hz, 1 H), 6.99 (m, 1 H), 6.75 (d, J=8.2 Hz, 1 H), 5.85 (d, J=5.3 Hz, 1 H), 4.83 (m, 1 H), 3.76 (s, 4 H), 3.5 (s, 2 H), 1.57 (s, 3 H), 1.35 (s, 3 H); $^{13}$C NMR (CDCl$_3$) 171.9, 156.6, 156.0, 140.7, 135.1, 132.9, 129.0, 126.3, 122.6, 119.4, 118.9, 118.2, 116.7, 102.9, 80.6, 71.7, 51.9, 49.7, 26.8, 19.2; IR (KBr) 1132.2, 1267.4, 1491.6, 1559.5, 1611.4, 1659.3, 1734.3, 2226.2, 2980.1, 3385.0 cm$^{-1}$. $[α]^{25}$D= −4.4° (c=0.525, DMF).

Anal calcd. for C$_{22}$H$_{23}$N$_3$O$_5$:

C, 64.54; H, 5.66; N, 10.26; Found: C, 64.36; H, 5.84; N, 10.01.

EXAMPLE 25

(3S-trans)-3-[[[(6-Cyano-3,4-dihydro-3-hydroxy-2,2-dimethyl-2H-1-benzopyran-4-yl) amino]carbonyl]amino]benzeneacetic acid A solution of (3S-trans)-3-[[[(6-cyano-3,4-dihydro-3-hydroxy-2,2-dimethyl-2H-1-benzopyran-4-yl) amino]carbonyl]amino]-benzeneacetic acid, methyl ester (0.7 g, 1.7 mmol, title compound from Example 24) in methanol (15 ml) under argon was treated with lithium hydroxide hydrate (0.14 g, 3.4 mmol) and the reaction was stirred at room temperature for 16 hours. More lithium hydroxide (two equivalent) was added and the reaction mixture was stirred for 48 hours. It was concentrated in vacuo and the residue was diluted with water (50 ml) and extracted with ethyl acetate. Organic layer was discarded and aqueous layer was acidified to pH∼1 with 10% hydrochloric acid and extracted with ethyl acetate (3×100 ml). It was washed with water (100 ml) and concentrated in vacuo. The residue was flash chromatographed on silica gel eluting with methylene chloride/methanol/acetic acid (1800:200:5) to give (3S-trans)-3-[[[(6-cyano-3,4-dihydro-3-hydroxy-2,2-dimethyl-2H-1-benzopyran-4-yl)amino]carbonyl]amino]benzeneacetic acid as a colorless solid (0.5 g, 73.9%), m.p. 135-138° C. (with foaming): $^1$H NMR (DMSO-d$_6$) δ 8.76 (s, 2 H), 7.62 (m, 2 H), 7.42 (m, 2 H), 7.25 (m, 2 H), 6.96 (d, J=8.3 Hz, 1 H), 6.90 (d, J=7.0 Hz, 1 H), 6.70 (d, J=8.2 Hz, 1 H), 4.77 (m, 2 H), 3.76 (m, 2 H), 1.51 (s, 3 H), 1.28 (s, 3 H); $^{13}$C NMR (CDCl$_3$) 172.8, 156.3, 155.9, 140.3, 135.6, 132.7, 132.4, 128.6, 126.0, 122.4, 119.1, 118.8, 117.9, 116.2, 102.7, 80.3, 71.6, 49.4, 26.5, 18.9; IR (KBr) 1132.1, 1267.2, 1491.3, 1559.3, 1611.2, 1659.3, 1713.2, 2228.1, 2980.1, 3379.0 cm$^{-1}$; $[α]^{25}$D= −6.7° (c=0.683, DMF).

Anal calcd. for C$_{21}$H$_{21}$N$_3$O$_5$.0.42 H$_2$O:

C, 62.59; H, 5.46; N, 10.43; Found: C, 62.97; H, 5.46; N, 10.05.

What is claimed is:

1. A compound of the formula

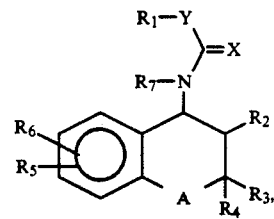

or pharmaceutically acceptable salts thereof, wherein A is —O—;

X is oxygen or sulfur,

Y is —NR$_8$;

R$_1$ is arylalkyl;

R$_2$ is hydrogen, hydroxy

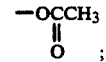

R$_3$ and R$_4$ are each independently hydrogen, alkyl or arylalkyl, or, R$_3$ and R$_4$ taken together with the carbon atom to which they are attached form a 5- to 7-membered carbocyclic ring;

R$_5$ is selected from H, alkyl, haloalkyl, alkenyl, alkynyl, cycloalkyl, arylalkyl, cycloalkylalkyl, —CN, —NO₂, —COR, —COOR, —CONHR, —CON(R)₂, —CF₃, S-alkyl, —SOalkyl, —SO₂alkyl,

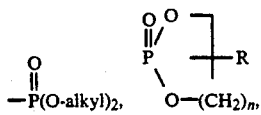

halogen, amino, substituted amino, O-alkyl, OCF₃, OCH₂CF₃, —OCOalkyl, —OCONRalkyl, —NRCOalkyl and NRCOOalkyl, NRCON(R)₂ wherein R in each of the above groups can be hydrogen, alkyl, aryl, arylkyl, cycloalkyl, or (cycloalkyl)alkyl or haloalkyl;

$R_6$ is selected from H, alkyl, halo, OH, O-alkyl, amino, substituted amino OCOalkyl, OCONRalkyl, NRCOalkyl, NRCOOalkyl and NRCON(R)₂ wherein R in each of the above groups can be hydrogen, alkyl, aryl, arylalkyl, cycloalkyl, (cycloalkyl)alkyl or haloalkyl;

$R_7$ and $R_8$ are each independently selected from hydrogen, alkyl and arylalkyl;

n is 1, 2 or 3.

2. The compound of claim 1 wherein
A is —O—;
X is O, S;
Y is NH;
$R_1$ is arylalkyl;
$R_2$ is hydroxy or hydrogen;
$R_3$ and $R_4$ are each alkyl;
$R_5$ is an electron withdrawing group;
$R_6$ is hydrogen, alkyl or O-alkyl; and,
$R_7$ is hydrogen.

3. The compound of claim 1 wherein
A is —O—;
X is O;
Y is NH;
$R_1$ is phenylmethyl;
$R_2$ is trans-hydroxy or hydrogen;
$R_3$ and $R_4$ are each methyl;
$R_5$ is —CN or —NO₂;
$R_6$ is hydrogen; and
$R_7$ is hydrogen.

4. A compound of claim 1 having the name N-(6-cyano-3,4-dihydro-2,2-dimethyl-2H-1-benzopyran-4-yl)-N'-phenylmethyl)urea.

5. A compound of claim 1 having the name (trans)-1-(6-(cyano-3,4-dihydro-3-hydroxy-2,2-dimethyl-2H-1-benzopyran-4-yl)-3-(phenylmethyl) urea.

6. A compound of claim 1 having the name (−)-N-(6-cyano-3.4-dihydro-2,2-dimethyl-2H-1-benzopyran-4-yl-N'-(phenylmethyl)urea.

7. A compound of claim 1 having the name (+)-N-(6-cyano-3.4-dihydro-2,2-dimethyl-2H-1-benzopyran-4-yl-N'-(phenylmethyl)urea.

* * * * *